(12) United States Patent
Müller-Hartmann et al.

(10) Patent No.: US 8,173,416 B2
(45) Date of Patent: May 8, 2012

(54) CIRCUIT ARRANGEMENT FOR INJECTING NUCLEIC ACIDS AND OTHER BIOLOGICALLY ACTIVE MOLECULES INTO THE NUCLEUS OF HIGHER EUCARYOTIC CELLS USING ELECTRICAL CURRENT

(75) Inventors: Herbert Müller-Hartmann, Köln (DE); Gudula Riemen, Langenfeld (DE); Kirsten Rothmann-Cosic, Berlin (DE); Corinna Thiel, Köln (DE); Ludger Altrogge, Pulheim (DE); Meike Weigel, Köln (DE); Rainer Christine, Köln (DE); Elke Lorbach, Köln (DE); Juliana Helfrich, Glauchau (DE); Heike Wessendorf, San Francisco, CA (US); Gregor Siebenkotten, Frechen-Königsdorf (DE)

(73) Assignee: Lonza Cologne GmbH, Cologne (DE)

( * ) Notice: Subject to any disclaimer, the term of this patent is extended or adjusted under 35 U.S.C. 154(b) by 1984 days.

(21) Appl. No.: 10/475,840

(22) PCT Filed: Apr. 23, 2002

(86) PCT No.: PCT/DE02/01489
§ 371 (c)(1),
(2), (4) Date: Mar. 15, 2004

(87) PCT Pub. No.: WO02/086129
PCT Pub. Date: Oct. 31, 2002

(65) Prior Publication Data
US 2004/0137603 A1    Jul. 15, 2004

(30) Foreign Application Priority Data

Apr. 23, 2001  (DE) .................................. 101 19 901

(51) Int. Cl.
| C12M 1/42 | (2006.01) |
| C12M 3/00 | (2006.01) |
| F41B 15/04 | (2006.01) |
| H01T 23/00 | (2006.01) |

(52) U.S. Cl. .................... 435/285.2; 435/461; 435/470; 435/173.1; 435/173.4; 435/173.5; 435/173.6; 435/288.3; 435/288.4; 435/288.5; 361/232

(58) Field of Classification Search .............. 435/285.2, 435/173.6, 461, 470, 173.1, 173.4, 173.5, 435/288.3, 288.4, 288.5; 361/232
See application file for complete search history.

(56) References Cited

U.S. PATENT DOCUMENTS
3,707,974 A    1/1973  Raddi
(Continued)

FOREIGN PATENT DOCUMENTS
DE    3718941    2/1988
(Continued)

OTHER PUBLICATIONS

Sukharev, S. I., "Electroporation and electrophoretic DNA transfer into cells", (1992) Biophys. J. 63, pp. 1320-1327.
(Continued)

*Primary Examiner* — Nathan Bowers
(74) *Attorney, Agent, or Firm* — Leydig, Voit & Mayer, Ltd.

(57) ABSTRACT

The invention relates to a novel circuit arrangement for electrotransfection or electrofusion, which enables the transportation of DNA and/or other biologically active molecules to the nucleus of higher eukaryotic cells or the fusion of cells, independent of cell division and with reduced cell mortality.

16 Claims, 19 Drawing Sheets

U.S. PATENT DOCUMENTS

Figure 1:
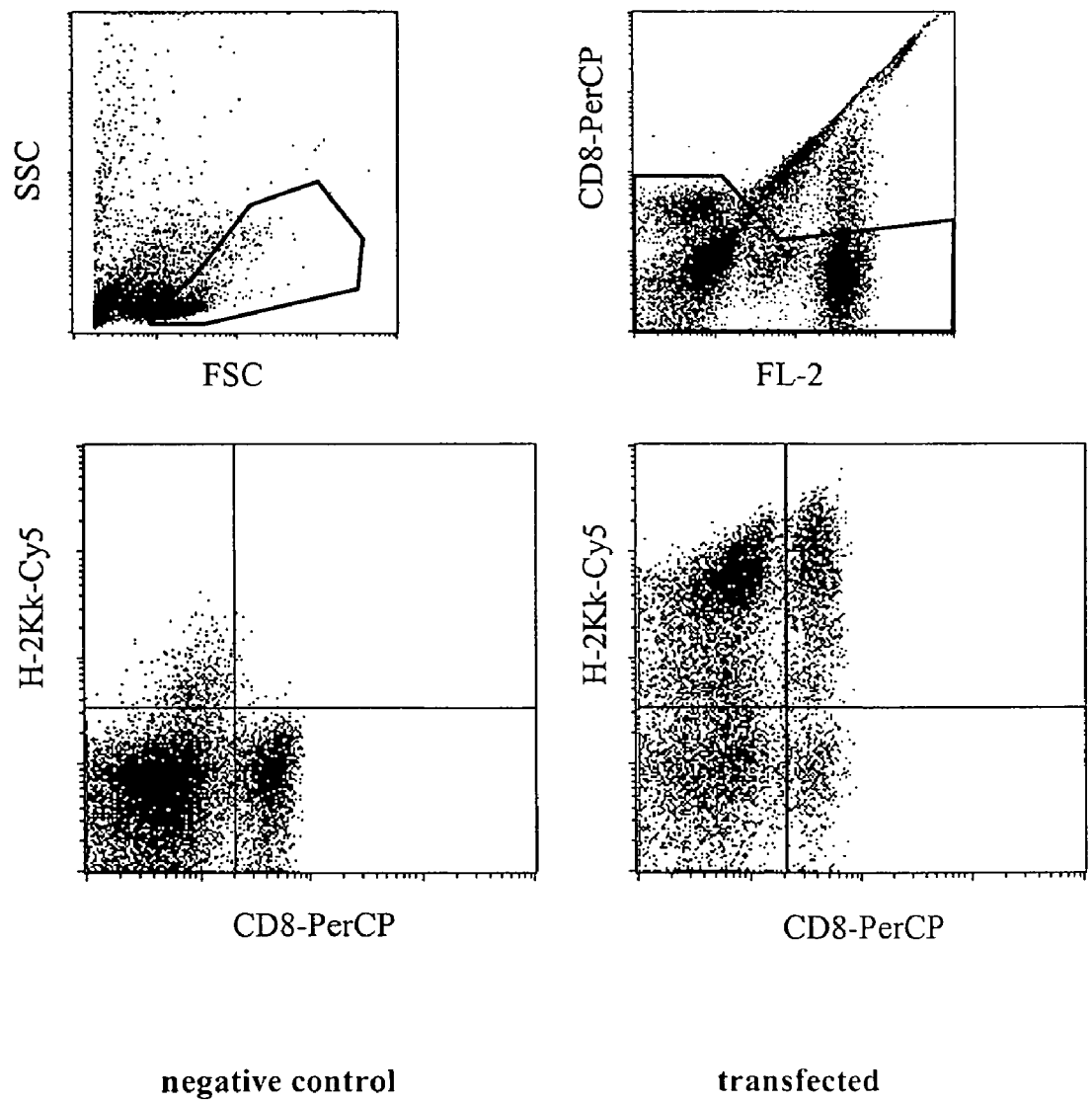

| | | | |
|---|---|---|---|
| 4,750,100 | A | 6/1988 | Ragsdale |
| 4,849,355 | A | 7/1989 | Wong |
| 4,906,576 | A | 3/1990 | Marshall, III |
| 4,923,814 | A | 5/1990 | Marshall, III |
| 4,946,793 | A | 8/1990 | Marshall, III |
| 4,959,321 | A | 9/1990 | Preece et al. |
| 5,098,843 | A | 3/1992 | Calvin |
| 5,128,257 | A | 7/1992 | Baer |
| 5,232,856 | A | 8/1993 | Firth |
| 5,254,081 | A | 10/1993 | Maurer et al. |
| 5,273,525 | A | 12/1993 | Hofmann |
| 5,422,272 | A | 6/1995 | Papp et al. |
| 5,627,023 | A | 5/1997 | Bolognesi |
| 5,642,035 | A | 6/1997 | Ragsdale |
| 5,869,326 | A | 2/1999 | Hofmann |
| 5,905,371 | A | 5/1999 | Limpaecher |
| 6,008,038 | A | 12/1999 | Kröger |
| 6,040,184 | A | 3/2000 | Greener |
| 6,103,084 | A | 8/2000 | Uhen |
| 6,150,148 | A | 11/2000 | Nanda |
| 6,258,592 | B1 * | 7/2001 | Ragsdale et al. ........... 435/285.2 |
| 6,521,430 | B1 | 2/2003 | Orwar |
| 6,632,672 | B2 | 10/2003 | Calos |

FOREIGN PATENT DOCUMENTS

| | | |
|---|---|---|
| DE | 3724291 A1 | 2/1989 |
| EP | 0113549 | 7/1984 |
| EP | 0283700 | 9/1988 |
| EP | 0362758 A2 | 4/1990 |
| EP | 0689289 A2 | 12/1995 |
| EP | 0866123 B1 | 9/1998 |
| EP | 1190075 B1 | 3/2002 |
| JP | 02035071 | 2/1990 |
| JP | 2303478 | 12/1990 |
| JP | 3195485 | 8/1991 |
| WO | WO-8802777 | 4/1988 |
| WO | WO91/18103 A1 | 11/1991 |
| WO | WO-9118103 | 11/1991 |
| WO | WO92/06185 A1 | 4/1992 |
| WO | WO95/35389 A1 | 12/1995 |
| WO | WO98/10515 A1 | 3/1998 |
| WO | WO99/36563 A1 | 7/1999 |

OTHER PUBLICATIONS

Brown, L. E., "Introduction of Exogenous DNA into Chlamydomonas reinhardtii by Electroporation" (1991) Molecular and Cellular Biol. 2328-32.

Leopold, R.A., "Using electroporation and a slot cuvette to deliver plasmid DNA etc" (1996) Genetic Anal.: Biomolecular Eng. 12:197-200.

Auer et al, Dielectric breakdown of the red blood cell membrane and uptake of SV40 DNA and mammalian RNA, Naturwissenschaften, 1976, vol. 63, p. 391.

Bamberger et al, "Dissociative Glucocorticoid Activity of Medroxyprogesterone Acetate in Normal Human Lymphocytes", Journal of Clinical Endocrinology & Metabolism, vol. 84, pp. 4055-4061.

Baubonis et al, "Genomic targeting with purified Cre recombinase", Nucleic Acids Research, vol. 21, No. 9, pp. 2025-2029, May 1993.

Bertling et al, "Intranuclear uptake and persistence of biologically active DNA after electroporation of mammalian cells", J. Biochem. Biophys. Methods, vol. 14(4), pp. 223-232 (1987).

Bertling, "Transfection of a DNA/protein complex into nuclei of mammalian cells using polyoma capsids and electroporation", Biosci. Rep., vol. 7, No. 2, pp. 107-112, Feb. 1987.

De Chasseval et al, "High level transient gene expression in human lymphoid cells by SV 40 large T antigen boost", Nucleic Acids Res., vol. 20 (2), pp. 245-250 (1992).

Edelstein et al, "Gene therapy clinical trials worldwide 1989-2004—an overview", J. Gene Med., vol. 6, No. 6, pp. 597-602, Jun. 2004.

Eurogentec, "Easyjet Plus User's Manual", Jul. 10, 1992, Eurogentec, Liege, XP002200115, pp. 1-27 and 30-39.

Kim et al, "Electroporation of extraneous proteins into CHO cells: increased efficacy by utilizing centrifugal force and microsecond electrical pulses", Exp. Cell Res., vol. 197(2), pp. 207-212 (1991).

Klenchin et al, "Electrically induced DNA uptake by cells is a fast process involving DNA electrophoresis", Biophys. J., vol. 60, No. 4, pp. 804-811, Oct. 1991.

Krueger et al, "Transient Transfection of Oligodendrocyte Progenitors by Electroporation", Neurochemical Research, 1998, vol. 23, pp. 421-426.

Lurquin, "Gene transfer by electroporation", Mol. Biotechnol., vol. 7(1), pp. 5-35, Feb. 1997.

Luo et al, "Synthetic DNA delivery systems", Nature Biotechnology, vol. 18, No. 1, pp. 33-37, Jan. 2000.

Marechal et al, "Mapping EBNA-1 domains involved in binding to metaphase chromosomes", J. Virol., vol. 73, pp. 4385-4392 (1999).

Neumann et al, "Permeability changes induced by electric impulses in vesicular membranes", J. Membrane Biol., vol. 10, pp. 279-290 (1972).

Neumann et al, "Gene transfer into mouse lyoma cells by electroporation in high electric fields", The EMBO Journal, vol. 1(7), pp. 841-845.

Palu et al, "In pursuit of new developments for gene therapy of human diseases", J. Biotechnol., vol. 68, No. 1, pp. 1-13, Feb. 1999.

Pliquett et al, "Determination of the electric field and anomalous heating caused by exponential pulses with aluminum electrodes in electroporation experiments", Bioelectrochemistry and Bioenergetics, vol. 39(1), pp. 39-53 (1996).

Potter et al, "Enhancer-dependent expression of human kappa immunoglobulin genes introduced into mouse pre-B lymphocytes by electroporation", Proc. Natl. Acad. Sci. USA, vol. 81(22), pp. 7161-7165 (1984).

Rols et al, "Ionic-strength modulation of electrically induced permeabilization and associated fusion of mammalian cells", Eur. J. Biochem., vol. 179, pp. 109-115 (1989).

Satoh et al, "Successful transfer of ADA gene in vitro into human peripheral blood CD34+ cells by transfecting EBV-based episomal vectors", FEBS Lett., vol. 441, No. 1, pp. 39-42, Dec. 1998.

Schwachtgen et al, "Optimization of the transfection of human endothelial cells by electroporation", Biotechniques, vol. 17(5), pp. 880-887 (1994).

Verma et al, "Gene therapy—promises, problems and prospects", Nature, vol. 389, No. 6648, pp. 239-242, Sep. 1997.

Watanabe et al, "Calcium phosphate-mediated transfection of primary cultured brain neurons using GFP expression as a marker: application for single neuron electrophysiology", Neuroscience Research, vol. 33, pp. 71-78 (1999).

Zimmermann et al, "Cells with manipulated functions: new perspectives for cell biology, medicine and technology", Angew. Chem. Int. Ed. Engl., vol. 20, pp. 325-344 (1981).

* cited by examiner

CD8-positive cytotoxic T-cells from human blood (74,3 % H-2Kk-positive)

negative control        transfected

Primary endothelial cells from human umbilical cord (49,7 % H-2Kk-positive)

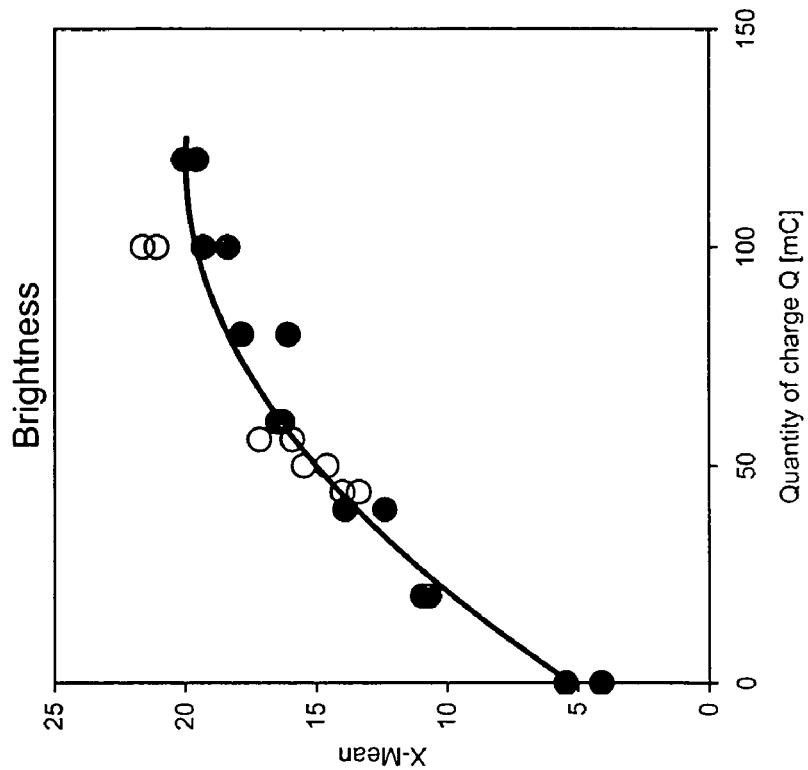
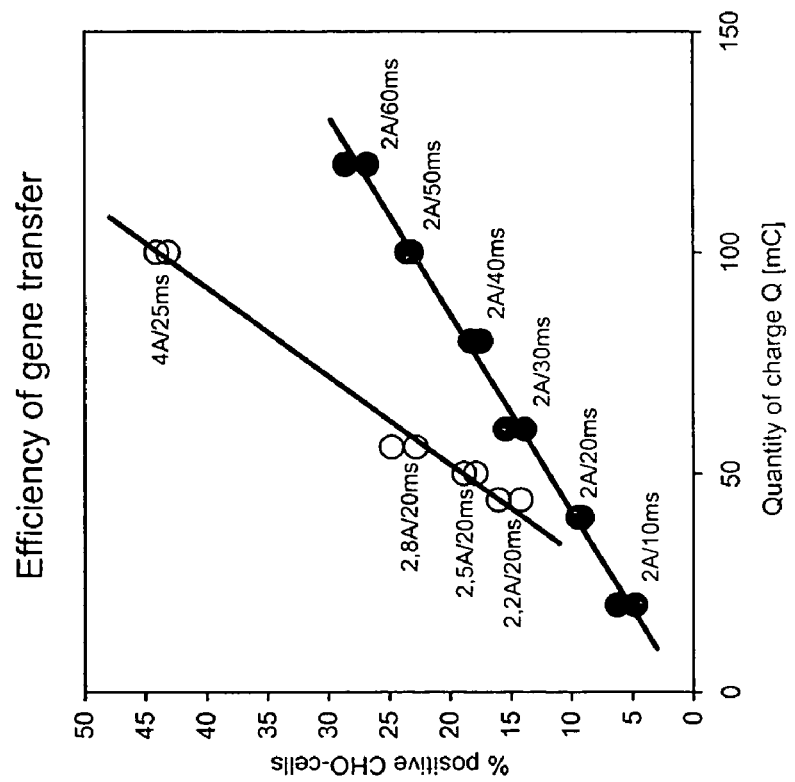
Fig. 7

CIRCUIT ARRANGEMENT FOR INJECTING NUCLEIC ACIDS AND OTHER BIOLOGICALLY ACTIVE MOLECULES INTO THE NUCLEUS OF HIGHER EUCARYOTIC CELLS USING ELECTRICAL CURRENT

The invention relates to a circuit arrangement for introducing nucleic acids, peptides, proteins and/or other biologically active molecules into the cell nucleus of eukaryotic cells by means of electric current, or for the treatment of cells, cell derivatives, subcellular particles and/or vesicles with electric current, consisting of at least two storage devices for quantities of electric charge, each supplied by a high-voltage power supply which each have at least one power semiconductor for transferring the quantities of charge present in the storage devices into a suspension in a cuvette and at least one monitoring device for controlling the power semiconductor.

BACKGROUND OF THE INVENTION

Since the place of action of eukaryotic DNA is the cell nucleus, DNA supplied from outside must enter the nucleus in order to be read out. Conventional transfection methods only bring about transport of DNA through the cell membrane into the cytoplasm. It is only because the nuclear membrane is temporarily dissolved during the cell division of higher eukaryotes that the DNA can passively enter the nucleus so that proteins encoded by it can be expressed. Only very small DNA molecules (oligonucleotides) can diffuse freely through the pores of the nuclear membrane. For the effective transfection of quiescent or weakly dividing cells it is thus necessary to create conditions which have the result that larger DNA molecules enter the nucleus through the nuclear membrane in sufficient quantity. The circuit arrangement described here makes this possible in higher eukaryotic cells.

STATE OF THE ART

It has been known for some time that DNA from a buffer can be introduced into cells with the aid of electric current. However, the circuit arrangements for electroporation described so far are based on the transport of DNA into the cytoplasm of higher eukaryotic cells so that the expression of transfected DNA remains dependent on the dissolution of the nuclear membrane during the cell division. None of the circuit arrangements for electroporation known so far is concerned with bringing DNA electrically specifically into the nucleus of higher eukaryotic cells. Thus, a circuit arrangement for electrotransfection optimised for electrical nucleus transport is not known.

U.S. Pat. No. 4,750,100 from Bio-Rad Laboratories, Richmond, USA (1986), describes a specific equipment structure which can provide a maximum of 3000 V at a maximum of 125 A by capacitor discharge.

U.S. Pat. No. 5,869,326 (Genetronics, Inc., San Diego, USA, 1996) describes a specific equipment structure by which means two, three or a plurality of pulses can be generated using two separate current sources. However it is not claimed or shown that these pulses have an effect which goes beyond the transport of DNA into the cytoplasm.

U.S. Pat. No. 6,008,038 and the European Patent Application EP 0 866 123 A1 (Eppendorf-Netheler-Hinz GmbH, Hamburg, 1998) describe a device with which short pulses of 10-500 µs and a maximum of 1.5 kV can be generated but again give no indication that certain conditions could lead to conveying DNA into the nucleus.

None of the circuit arrangements known so far is optimised to make it possible for DNA and/or other biologically active molecules to be effectively transported into the cell nucleus with low cell mortality.

The object of the invention is to provide a circuit arrangement which makes it possible for DNA and/or biologically active molecules to be transported effectively into the cell nucleus with low cell mortality.

DESCRIPTION OF THE INVENTION

In order to solve the object according to the invention it is provided that the first storage device is charged with the preset voltage ($U_1$) as a parameter and the second storage device is charged with a voltage $U_2 = R \times I_2 \times K_2$, wherein R is the resistance of the cuvette and the suspension contained therein, $I_2$ is the desired current and $K_2$ is a correction value which takes into account the cuvette properties and wherein at least one first pulse with the capacitor voltage ($U_1$) of the storage device can be transferred to the cell for a preset time ($T_1$) by controlling a power semiconductor.

In a development of the invention it is provided that without interruption at least one second pulse with the capacitor voltage ($U_2$) of the storage device can also be applied to the cuvette by controlling a power semiconductor, wherein the delivered quantity of charge in at least one selectable time interval can be measured by the monitoring device, wherein the preset desired quantity of charge is compared with the actual delivered quantity of charge and on reaching or exceeding the desired quantity of charge, the power semiconductor is blocked.

In addition to the possibility of determining the delivered quantity of charge using the current flowing from the storage device, alternatively the preset desired quantity of charge is compared with the actual delivered quantity of charge in an interval of time and on reaching or exceeding the desired quantity of charge, the power semiconductor is blocked. On this occasion, depending on the pulse shape used and the number of pulses, the time interval which can be selected for the determination can be individually predefined in order, for example, to determine the delivered quantity of charge during the first or each subsequent pulse. The delivered quantity of charge can be determined by determining the difference between the original charge at least of one of the storage devices and the residual charge. In this case it is possible that according to the number of pulses used, more than one of the at least two storage devices is used in a circuit fashion wherein each storage device is assigned at least one high-voltage power supply, a monitoring device and a power semiconductor to transfer the quantity of charge to the cuvette containing the cell suspension. For the pulse transfer it is provided that the first power semiconductor transfers a pulse of 2-10 kV/cm having a duration of 10-100 µs and a current density of at least 2 A·cm$^2$ and, without interruption, the second power semiconductor transfers a pulse having a current density of 2-14 A·cm$^2$ and a maximum duration of 100 ms. The time interval for determining the delivered quantity of charge can consequently be specified with the delivery of a first and/or preferably a second or each further pulse.

The delivered quantity of charge of the second pulse is preferably monitored wherein the switch-on time ($T_2$) of the second pulse can be specified by comparing the desired quantity of charge with the actual quantity of charge delivered by the measurement time and ends when the desired quantity of charge is reached and wherein a measurement cycle of 1 msec is provided to determine the actual quantity of charge, wherein during the time ($T_2$) the capacitor voltage decreases exponentially and the power semiconductor can be blocked on reaching the specified quantity of charge ($Q_2$).

Alternatively it is possible that after at least one predetermined time interval after triggering a first and/or second pulse, the flowing current is measured and if this exceeds or falls below a desired value, the pulse duration can be re-adjusted in order to keep the delivered quantity of charge constant. In another alternative it is possible that after at least one predetermined time interval after triggering a first and/or second pulse, the flowing current is measured and if this exceeds or falls below a desired value, an error message is generated to give a warning to the user of the device. It is furthermore possible that after at least one predetermined time interval after triggering a first and/or second pulse, the flowing current is measured and if this exceeds or falls below a desired value, the desired value is readjusted.

In order to determine any necessary constants, especially of the cuvette used with the cell suspension, it can be provided that a preliminary measurement of the resistance of the cuvette with the cell suspension is made. The other necessary pulse parameters are preferably pre-selected manually or if necessary specified by entering a code. It is thus also possible to use retrievable data via a card reader. The card reader can also be used at the same time to store the time profile of the voltage applied to the cuvette or the current flowing through the cuvette for documentation purposes for one or a plurality of pulse delivery processes on a commercially available memory card. This memory card is preferably used at the same time for storing the pulse parameters to be set.

As a result of the circuit regulation of the pulse delivery, the transfer of the envisaged quantity of charge is thus monitored in a reliable and advantageous fashion at least for one pulse and a controlled and sample-dependent transfer of a preset quantity of charge as well as a controlled monitoring to avoid any damage to the cells located in the sample can be achieved.

For further safety of the user and the samples used it is provided that an overcurrent cutoff is provided for the first and each subsequent pulse. The overcurrent cutoff thus allows the high-voltage pulse to be interrupted at any time in the event that preset limiting values are exceeded.

The high-voltage pulse of 2-10 kV/cm described is suitable for creating conditions such that DNA can enter the cell nucleus independently of the cell division. In order to keep cell damage low, this pulse is limited to between 10 and a maximum of 200 µs, preferably 10-50 µs. This is sufficient to achieve transfection independent of cell division. For example, such a short single high-voltage pulse was found to be optimum for the transfection of endothelial cells from the human umbilical vein. Another current pulse of lower field intensity or lower current strength or current density but of longer duration, following without interruption influences the efficiency of the transfection. As a result of the significantly lower current density, this pulse can persist significantly longer with little cell damage. An optimum current density or duration of the second pulse is obtained depending on the cell type and sensitivity of the cell. Such combined pulses are found to be optimal, for example, for primary human dermal fibroblasts or melanocytes or various human blood cells. In experiments using different cell lines and expression systems, the following was shown: the higher the current density of the second pulse, the stronger its influence on the transfection rate, i.e. the percentage of transfected cells. The lower the current density, the more the second pulse causes pure DNA transport into cells already transfected by the first pulse. The expression level of the transfected cells increases with increasing pulse duration but not the fraction of transfected cells. In order to maintain a precise cell-specific control of the transfection rate, the expression level and the cell vitality, the pulse duration and current density of the second pulse must therefore be controlled.

In order to achieve precise control of the pulse actually delivered to the cell suspension, in a preferred embodiment the delivered quantity of charge is controlled. In order to control the current strength or current density by a selectable capacitor voltage of the storage unit, the resistance of the cuvette and the cell suspension contained therein must be predefined initially. It was found that the resistance of the cuvettes when using aluminium electrodes varies during the pulse as a result of electrochemical processes. This variation is taken into account by a pulse-specific predefined correction value. Thus, precise pulse shapes for the second pulse can be predetermined using $U_2 = R \times I_2 \times K_2$ by controlling the charge, where $U_2$ is the capacitor voltage with which the storage device is charged, R is the resistance of the cuvette and the cell suspension contained therein, $I_2$ is the desired current and $K_2$ is the pulse-specific correction value.

In one embodiment of the invention the ohmic cuvette resistance R can be measured directly before the beginning of pulse delivery by applying a test voltage and taken into account accordingly in the calculation of the voltage $U_2$. Since the resistance measured before pulse delivery is subjected to larger fluctuations than the resistance during pulse delivery, presumably as a result of electrochemical processes, it is found to be advantageous to fixedly predefine the resistance R to calculate the capacitor voltage $U_2$ as a parameter. In a preferred embodiment of the invention the resistance of the cuvette is measured before the commencement of pulse delivery regardless of this in order to determine whether this lies within a predefined resistance window. If the measured resistance lies outside this window, there is a fault and the pulse delivery is not released.

For every cell type optimum conditions can be established for transfection rate, transfection intensity and cell vitality. In a preferred embodiment of the circuit arrangement the field intensity and duration of the first pulse and initial current intensity or current density and empirical duration of the second pulse can be selected and optimum conditions can simply be established for various cell types via a code.

The circuit arrangement can be used in an advantageous fashion for the transfection of quiescent or dividing eukaryotic cells. In the same way the circuit arrangement is also suitable for the transfection of primary cells such as human blood cells, pluripotent precursor cells from human blood, primary human fibroblasts, endothelial cells, muscle cells or melanocytes and can be used for diagnostic purposes or for the manufacture of a medicinal product for ex-vivo gene therapy.

The circuit arrangement according to the invention is furthermore also suitable, for example, for electrofusion, i.e., methods for the fusion of cells, cell derivatives, subcellular particles and/or vesicles by means of electric current, wherein, for examples the cells, cell derivatives, subcellular particles and/or vesicles are initially suspended in a suitable density in an aqueous solution, the suspension is then transferred to a cuvette and finally an electric voltage is applied to the electrodes of the cuvette and a current flow is generated through the suspension. Alternatively, for example, adherent cells, cell derivatives, subcellular particles and/or vesicles or however, also adherent cells with suspended cells, cell derivatives, subcellular particles or vesicles can be fused.

The circuit arrangement described here generates very high field intensities of 2 to 10 kV/cm which have the effect that DNA and/or biologically active molecules can enter the nucleus independently of the cell division. These field intensities are far above those normally used for electroporation and far beyond those sufficient for efficient opening of the pores in the cell membrane (on average 1 kV/cm according to Lurquin, 1997, Mol. Biotechnol. 7, 5).

The subject matter of the invention is thus a circuit arrangement for implementing a method for introducing nucleic acids, peptides, proteins and/or other biologically active molecules into the cell nucleus of higher eukaryotic cells using electric current wherein the introduction into the nucleus is achieved by a pulse having a field intensity 2-10 times that sufficient for opening the pores in the cell membrane and a duration of at least 10 µs and a current density of at least 2 A·cm$^2$.

The introduction of nucleic acids, peptides, proteins and/or other biologically active molecules into the cell nucleus can be achieved by a pulse of 2-10 kV/cm, preferably 3-8 kV/cm, wherein the pulse is a maximum of 200 µs long.

The circuit arrangement is designed so that the first pulse can be followed without interruption by a current flow having a current density of 2 A·cm$^{-2}$ up to a maximum of 14 A·cm$^2$, preferably up to 5 A·cm$^2$, of 1 ms up to a maximum of 100 ms, preferably up to 50 ms in length.

Since the circuit arrangement makes transfection possible regardless of the cell division, in addition to dividing cells, quiescent or weakly dividing primary cells can also be transfected.

In other preferred embodiments the higher eukaryotic cells comprise primary human fibroblasts, endothelial cells and melanocytes.

The eukaryotic cells transfected using the circuit arrangement according to the invention can also be used for diagnostic and analytic purposes to produce a pharmaceutical product for ex-vivo gene therapy.

The circuit arrangement according to the invention makes it possible to achieve transfection independent of cell division and thus to considerably speed up transfection experiments. In transfection experiments using expression vectors, an analysis according to promoter and expressed protein can be made even a few hours after the transfection.

The concept "biologically active molecules" means peptides, proteins, polysaccharides, lipids or combinations or derivatives of these molecules as long as they develop a biological affinity in the cell.

Electroporation buffers having a high ionic strength and high buffer capacity are especially suitable for use with the circuit arrangement according to the invention.

The following protocol can be used to introduce nucleic acids into the cell nucleus of eukaryotic cells: 1×10$^5$-1×10$^7$ cells and up to 10 µg DNA are incubated in 100 µl electroporation buffer in a cuvette having a 2 mm interelectrode gap for 10 min at room temperature and then transfected according to the conditions according to the invention. Immediately afterwards the cells are washed out of the cuvette with 400 µl of cell culture medium and incubated for 10 min at 37° C. The cells are then plated out in 37° C. warm cell culture medium.

Suitable cuvettes are commercially available cuvettes for the electroporation of prokaryotes having an interelectrode gap or 2 mm or 1 mm, for example.

Evidence that the nucleic acids enter the cell nucleus independently of cell division can be furnished by analysing the cells which have not divided between transfection and analysis. This is achieved on the one hand by the transfection of non-dividing cells, such as for example cells of peripheral human blood and on the other hand for dividing cells by an analysis a few hours after transfection at a time when at most a fraction of the cells can have divided The following abbreviations are used in addition to those in general use:

| FACS | Fluorescence activated cell sorting |
|------|--------------------------------------|
| FCS  | Foetal calf serum |
| PBMC | Peripheral blood mononuclear cells |
| PE   | Phycoerythrin |

EXAMPLES

The following examples illustrate the invention but should not be regarded as restrictive.

Example 1

Transfection of Cytotoxic T Cells From Human Blood

Freshly prepared unstimulated (non-dividing) mononuclear cells from peripheral human blood (PBMC) were transfected with a vector which codes for the heavy chain of the mouse MHC class 1 protein H-2K$^k$. 5×10$^6$ cells together with 5 µg of vector DNA in a buffer having a high buffer capacity (48 mM×pH$^{-1}$) and high ionic strength (280 mM) were placed at room temperature in a cuvette having a 2 mm interelectrode gap and transfected by a 1000 V pulse of 100 µs duration, followed by a current flow having a current density of 5 A·cm$^{-2}$ and 40 ms. Immediately afterwards, the cells were washed from the cuvette using 400 µl of culture medium, incubated for 10 minutes at 37° C. and then transferred to a culture dish with pre-heated medium. After incubating for 24 h, the cells were successively incubated with digoxigenin-coupled anti-H-2K$^k$-antibody and Cy5-coupled anti-digoxigenin-antibody, as well as with a PerCP-coupled anti-CD8-antibody to identify human cytotoxic T cells and analysed using a flow cytometer (FACScalibur, Becton Dickinson). The number of dead cells was determined by staining with propidium iodide. As shown in FIG. 1, 74.3% of the living cells express the H-2K$^k$ antigen which corresponds to a very high transfection efficiency.

Example 2

Transfection of Human Haematopoeitic Stem Cells (CD34)

Figure 2:
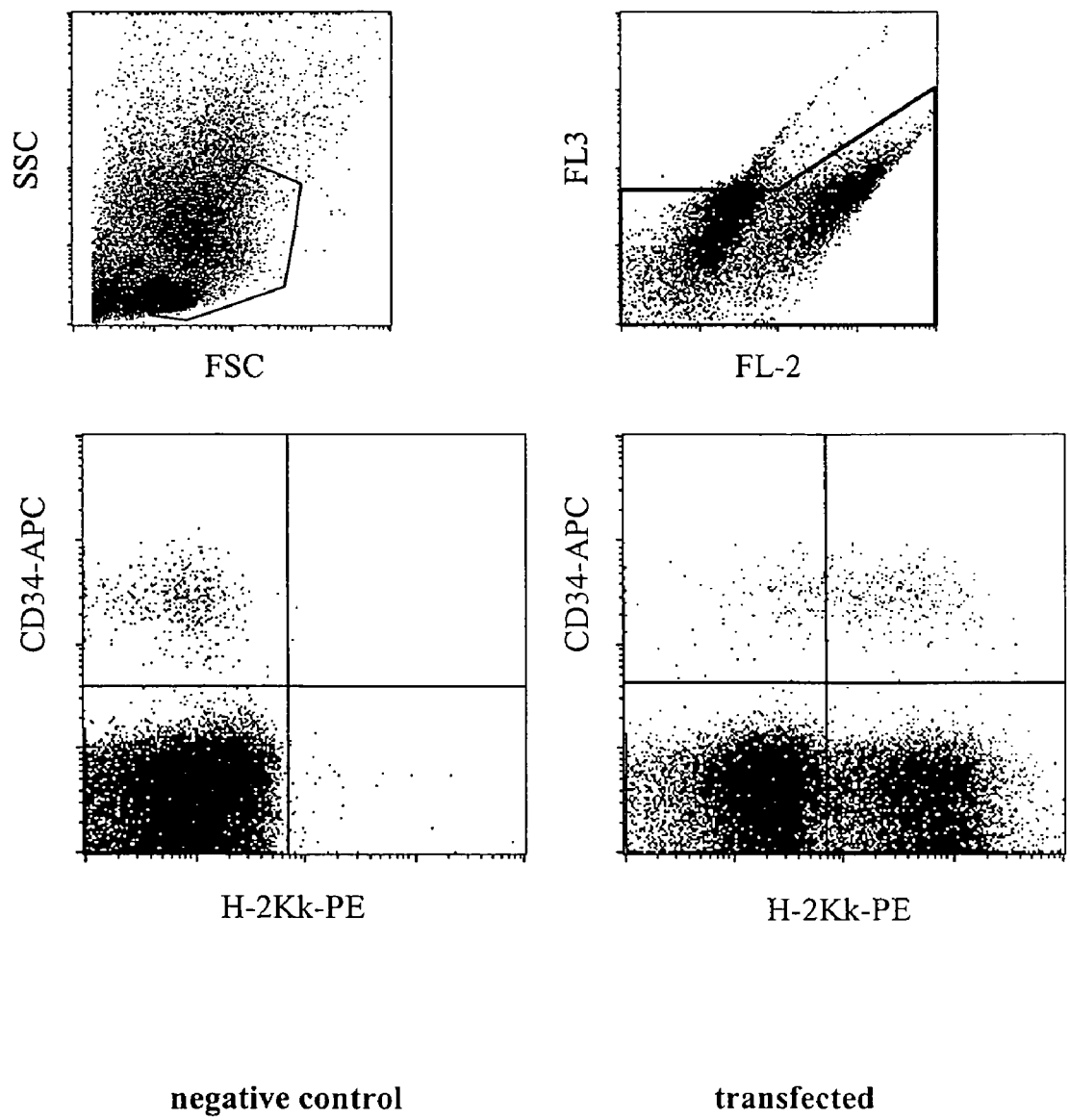

CD34-positive cells were pre-enriched from freshly prepared PBMC described as in Example 1 by magnetic cell sorting. Respectively 1×10$^4$ CD34-positive cells were then mixed with 1×10$^6$ PBMCs, placed together with 5 µg H-2K$^k$-expression vector DNA in a buffer having a high buffer capacity (54 mM×pH$^{-1}$) and high ionic strength (260 mM) at room temperature in a cuvette having a 2 mm interelectrode gap and transfected by a 1000 V pulse of 100 µs duration, followed by a current flow having a current density of 4 A·cm$^{-2}$ and 20 ms duration. Immediately afterwards, the cells were washed from the cuvette using 400 µl of culture medium, incubated for 10 minutes at 37° C. and then transferred to a culture dish with pre-heated medium. After incubating for 16 h, the cells were successively incubated with phycoerythrin-coupled anti-H-2K$^k$-antibody, as well as with an APC-coupled anti-CD34 antibody to identify human haematopoietic stem cells and analysed using a flow cytometer (FACScalibur, Becton Dickinson). The number of dead cells was determined by staining with propidium iodide. As shown in FIG. 2, 66.7% of the cells express the H-2K$^k$ antigen which corresponds to a high transfection efficiency.

Example 3

Transfection of Human Neonatal Dermal Fibroblasts (NHDF-Neo)

Figure 3:
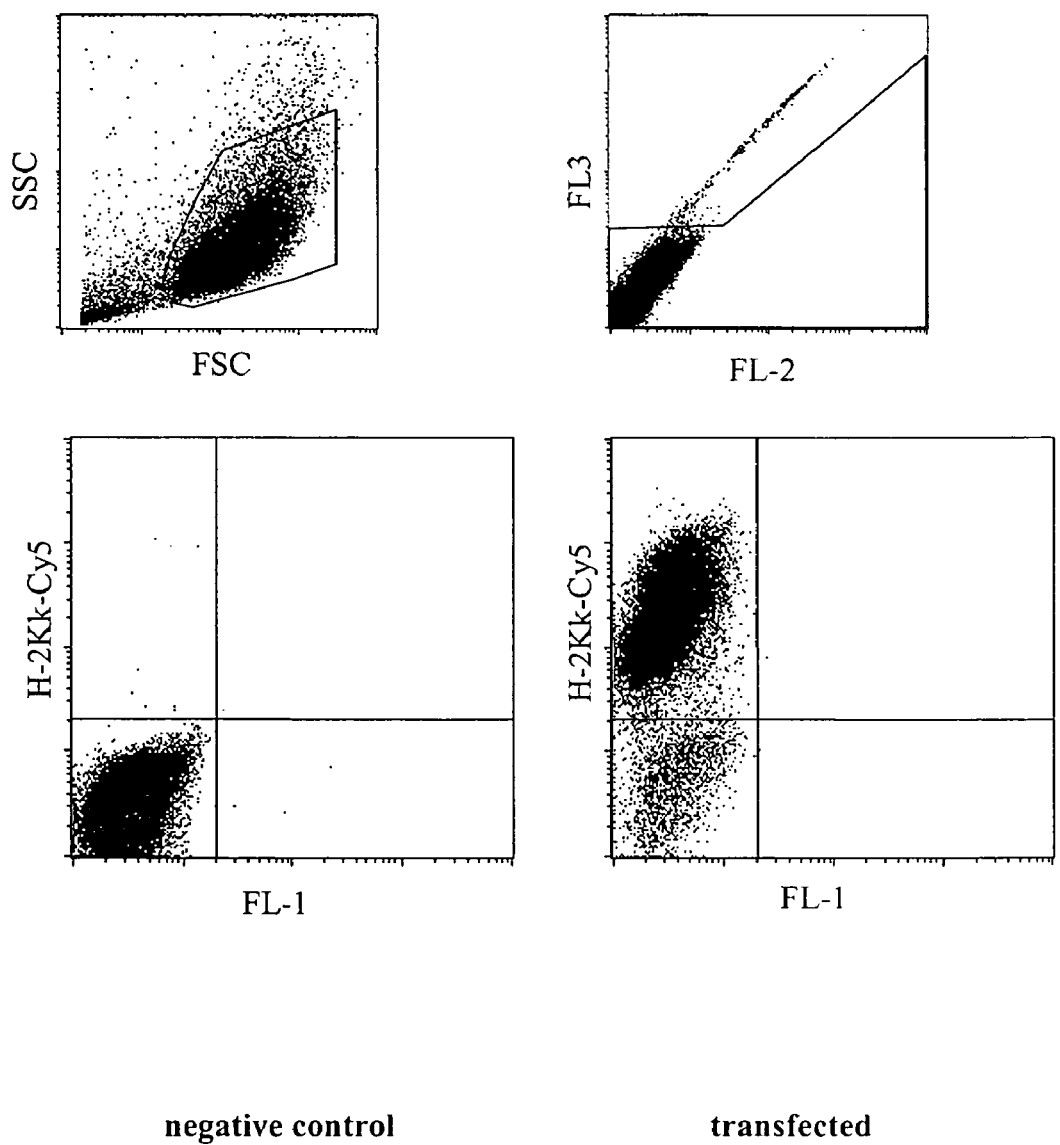

Human neonatal dermal fibroblasts ($5\times10^5$ cells) together with 5 μg H-2K$^k$-expression vector DNA were placed in a buffer having a high buffer capacity (67 mM×pH$^{-1}$) and high ionic strength (380 mM) at room temperature in a cuvette having a 2 mm interelectrode gap and transfected by a 1000 V pulse of 100 μs duration, followed by a current flow having a current density of 6 A·cm$^{-2}$ and of 33 ms duration. Immediately afterwards, the cells were washed from the cuvette using 400 μl of culture medium, incubated for 10 minutes at 37° C. and then transferred to a culture dish with pre-heated medium. After incubating for 5 h, the cells were incubated with a Cy5-coupled anti-H-2K$^k$-antibody and analysed using a flow cytometer (FACScalibur, Becton Dickinson). The number of dead cells was determined by staining with propidium iodide. As shown in FIG. 3, 93% of the cells express the H-2K$^k$ antigen which corresponds to a very high transfection efficiency.

Example 4

Transfection of Human Neonatal Melanocytes

Figure 4:
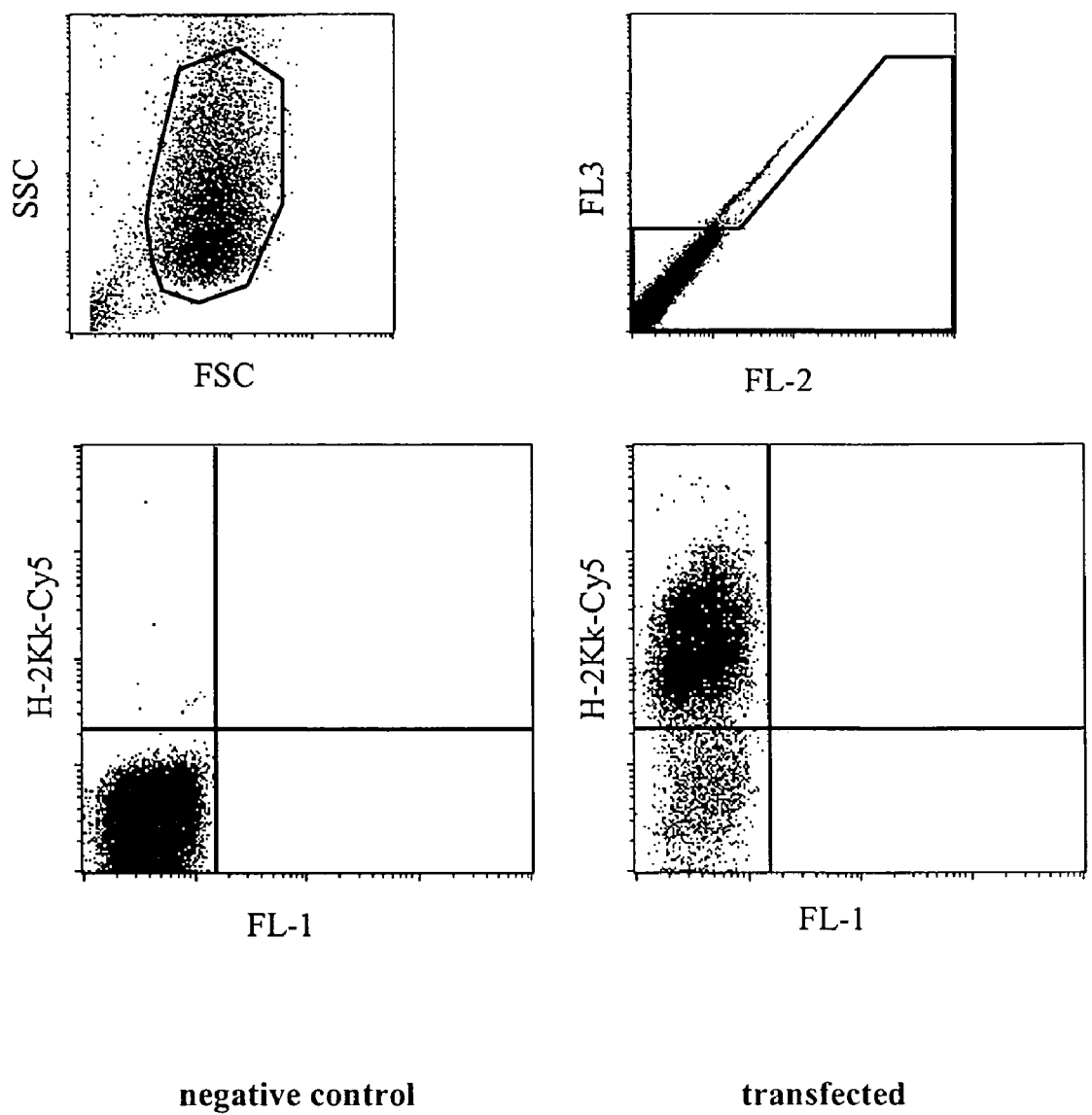

Human neonatal melanocytes ($2.5\times10^5$ cells) together with 5 μg H-2K$^k$-expression vector DNA were placed in a buffer having a high buffer capacity (54 mM×pH$^{-1}$) and high ionic strength (260 mM) at room temperature in a cuvette having a 2 mm interelectrode gap and transfected by a 1000 V pulse of 100 μs duration, followed by a current flow having a current density of 6 A·cm$^{-2}$ and 33 ms duration. Immediately afterwards, the cells were washed from the cuvette using 400 μl of culture medium, incubated for 10 minutes at 37° C. and then transferred to a culture dish with pre-heated medium. After incubating for 5 h, the cells were incubated with a Cy5-coupled anti-H-2K$^k$-antibody and analysed using a flow cytometer (FACScalibur, Becton Dickinson). The number of dead cells was determined by staining with propidium iodide. As shown in FIG. 4, 75.1% of the cells express the H-2K$^k$ antigen which corresponds to a very high transfection efficiency.

Example 5

Transfection of Human Endothelial Cells From the Umbilical Vein (HUVEC)

Figure 5:
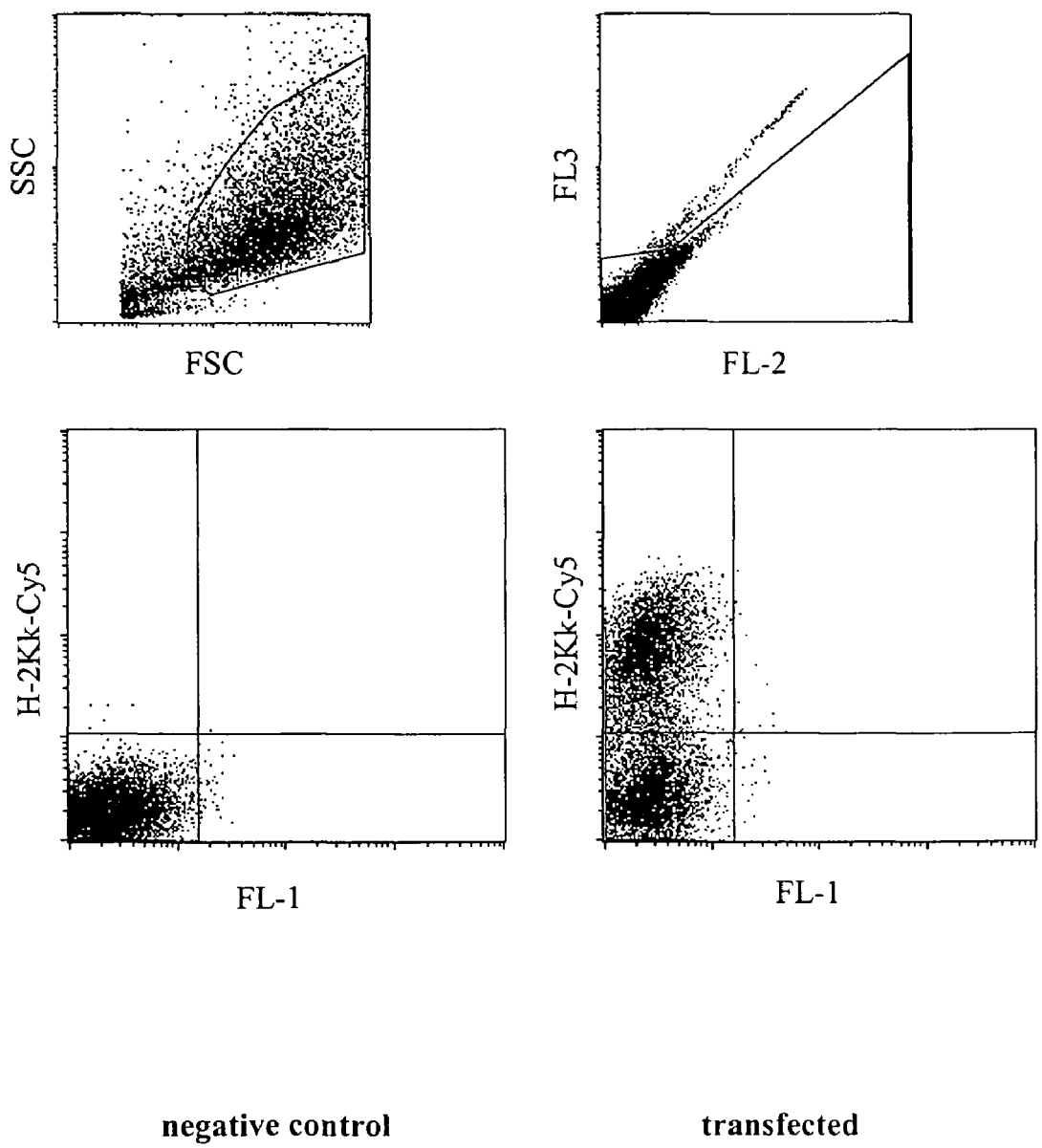

Endothelial cells from the human umbilical vein ($1\times10^6$ cells) together with 5 μg H-2K$^k$-expression vector DNA were placed in a buffer having a high buffer capacity (67 mM×pH$^{-1}$) and high ionic strength (378 mM) at room temperature in a cuvette having a 2 mm interelectrode gap and transfected by a 1000 V pulse of 100 μs duration. Immediately afterwards, the cells were washed from the cuvette using 400 μl of culture medium, incubated for 10 minutes at 37° C. and then transferred to a culture dish with pre-heated medium. After incubating for 5 h, the cells were incubated with a Cy5-coupled anti-H-2K$^k$-antibody and analysed using a flow cytometer (FACScalibur, Becton Dickinson). The number of dead cells was determined by staining with propidium iodide. As shown in FIG. 5, 49.7% of the cells express the H-2K$^k$ antigen which corresponds to a high transfection efficiency.

Example 6

Transfection of the Human Cell Line K562

Figure 6:
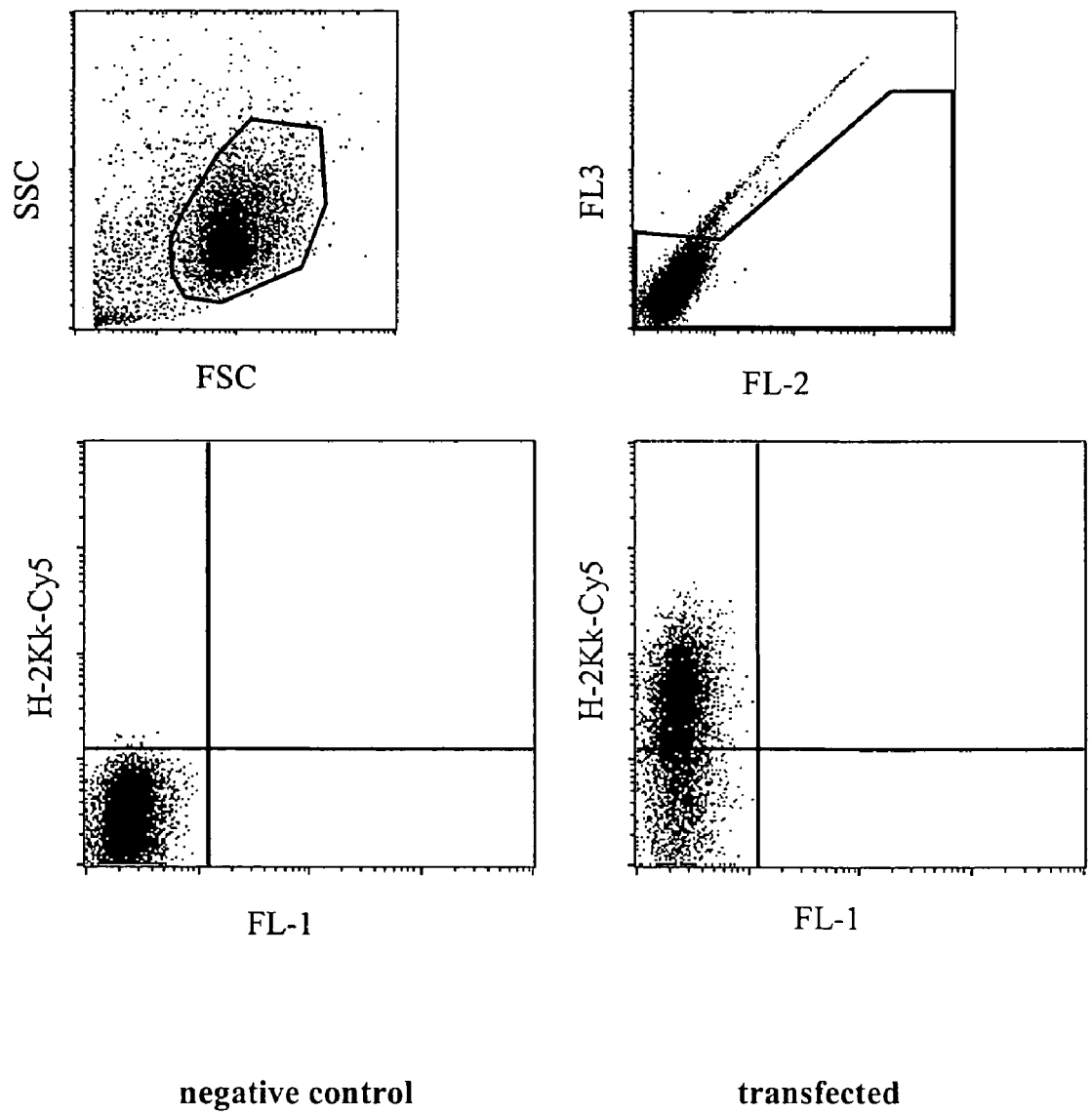

K562 cells ($1\times10^6$ cells) together with 5 μg H-2K$^k$-expression vector DNA were placed in a buffer having a high buffer capacity (24 mM×pH$^{-1}$) and high ionic strength (254 mM) at room temperature in a cuvette having a 2 mm interelectrode gap and transfected by a 1000 V pulse of 100 μs duration, followed by a current flow having a current density of 8 A·cm$^{-2}$ and 10 ms duration. Immediately afterwards, the cells were washed from the cuvette using 400 μl of culture medium, incubated for 10 minutes at 37° C. and then transferred to a culture dish with pre-heated medium. After incubating for 4 h, the cells were incubated with a Cy5-coupled anti-H-2K$^k$-antibody and analysed using a flow cytometer (FACScalibur, Becton Dickinson). The number of dead cells was determined by staining with propidium iodide. As shown in FIG. 6, 69.5% of the cells express the H-2K$^k$ antigen which corresponds to a very high transfection efficiency.

Example 7

Transfection Efficiency and Average Fluorescence Intensity of Cycle3-GFP-Transfected CHO Cells In order to investigate the transfection efficiency and the average fluorescence intensity of transfected cells as a function of the quantity of charge flowing in the second pulse, respectively $7\times10^5$ CHO cells together with 5 μg Cycle3-GFP-vector-DNA were placed in electroporation buffer in a cuvette having an interelectrode gap of 2 mm and transfected by a 1000 V, 10 μs pulse and subsequent second pulses differing in the variation of the current intensity or current density and pulse time. After cultivation for 5 hours, the cells were analysed using a flow cytometer. FIG. 7 shows the transfection efficiency determined as a function of the integral of the current over the pulse time (the quantity of charge Q). It is found that the transfection efficiency can be increased with increasing current intensity (open circles). An increase in the pulse time for the same current intensity on the other hand results in no appreciable increase in efficiency (closed circles). The fluorescence intensity (brightness) of the transfected cells increases with increasing quantity of charge Q, with saturation being reached for high Q. No major differences are found whether the increase in Q was achieved by increasing the current intensity (open circles) or increasing the pulse length (closed circles).

Example 8

Figure 8:
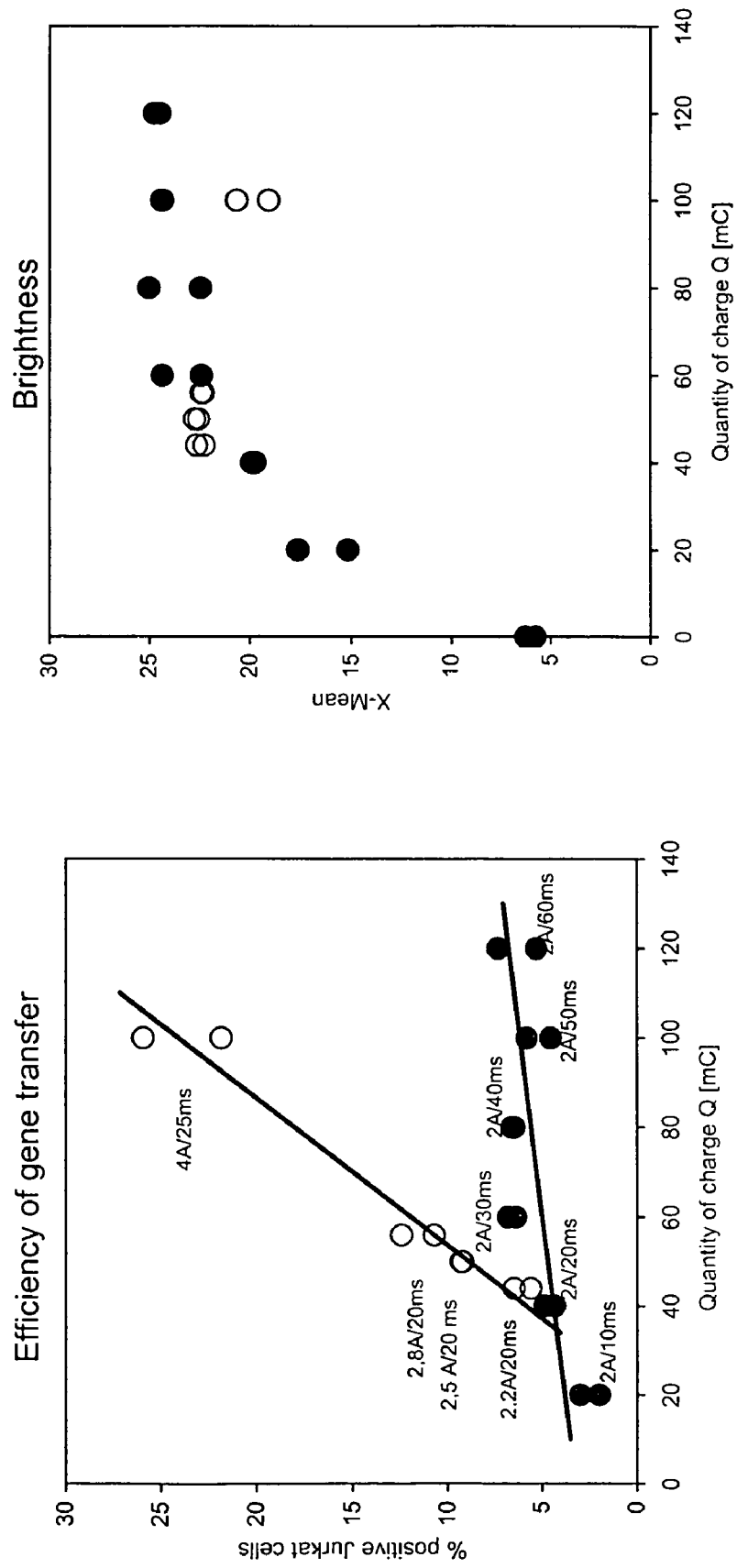

Transfection Efficiency and Average Fluorescence Intensity of Cycle3-GFP-Transfected Jurkat Cells In order to investigate the transfection efficiency and the average fluorescence intensity of transfected cells as a function of the quantity of charge flowing in the second pulse, respectively $4\times10^5$ Jurkat cells together with 5 μg Cycle3-GFP-vector-DNA were placed in electroporation buffer in a cuvette having an interelectrode gap of 2 mm and transfected by a 1000 V, 10 μs pulse and subsequent second pulses differing in the variation of the current intensity or current density and pulse time. After cultivation for 5 hours, the cells were analysed using a flow cytometer. FIG. 8 shows the transfection efficiency determined as a function of the integral of the current over the pulse time (the quantity of charge Q). As when using CHO cells, it is found that the transfection efficiency can be increased with increasing current intensity (open circles). An increase in the pulse time for the same current intensity on the other hand results in no appreciable increase in efficiency (closed circles). The fluorescence intensity (brightness) of the transfected cells increases with increasing quantity of charge Q, with saturation being reached for high Q. No major differences are found whether the increase in Q was achieved by increasing the current intensity (open circles) or increasing the pulse length (closed circles).

Example 9

Transfection Efficiency and Average Fluorescence Intensity of H-2K$^k$-Transfected Jurkat Cells

Figure 9:
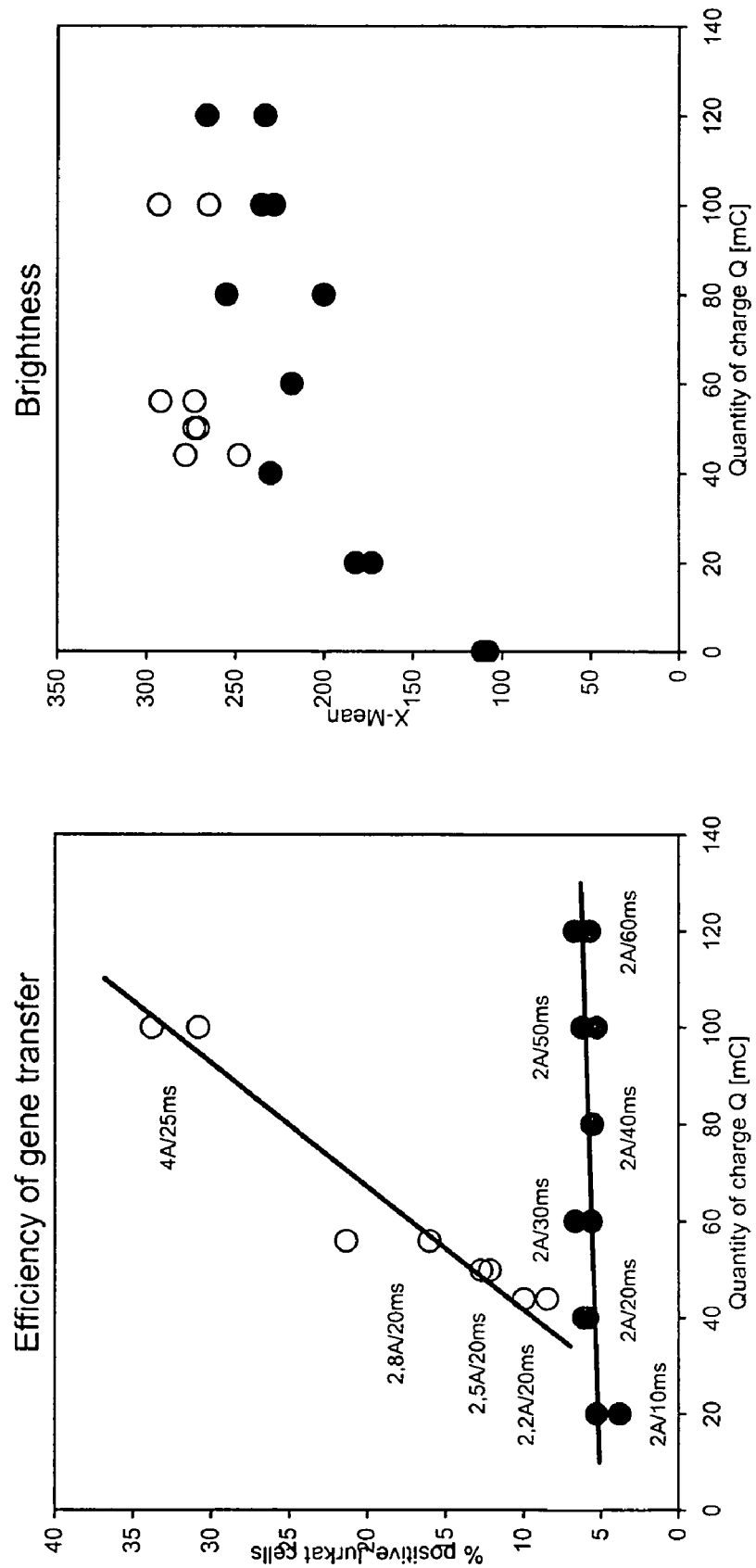

In order to investigate the transfection efficiency and the average fluorescence intensity of transfected cells as a function of the quantity of charge flowing in the second pulse, respectively 1×10$^6$ Jurkat cells together with 2 μg of H2K$^k$-expression vector DNA were placed in electroporation buffer in a cuvette having an interelectrode gap of 2 mm and transfected by a 1000 V, 10 μs pulse and subsequent second pulses differing in the variation of the current intensity or current density and pulse time. After cultivation for 3.5 hours, the cells were incubated with Cy5-coupled anti-H2K$^k$ and analysed using a flow cytometer. FIG. 9 shows the transfection efficiency determined as a function of the integral of the current over the pulse time (the quantity of charge Q). It is found that the transfection efficiency can be increased with increasing current intensity (open circles). An increase in the pulse time for the same current intensity on the other hand results in no appreciable increase in efficiency (closed circles). The fluorescence intensity (brightness) of the transfected cells increases with increasing quantity of charge Q, with saturation being reached for high Q. No major differences are found whether the increase in Q was achieved by increasing the current intensity (open circles) or increasing the pulse length (closed circles).

The invention is explained further with reference to the following figures.

In the figures

Figure 10:
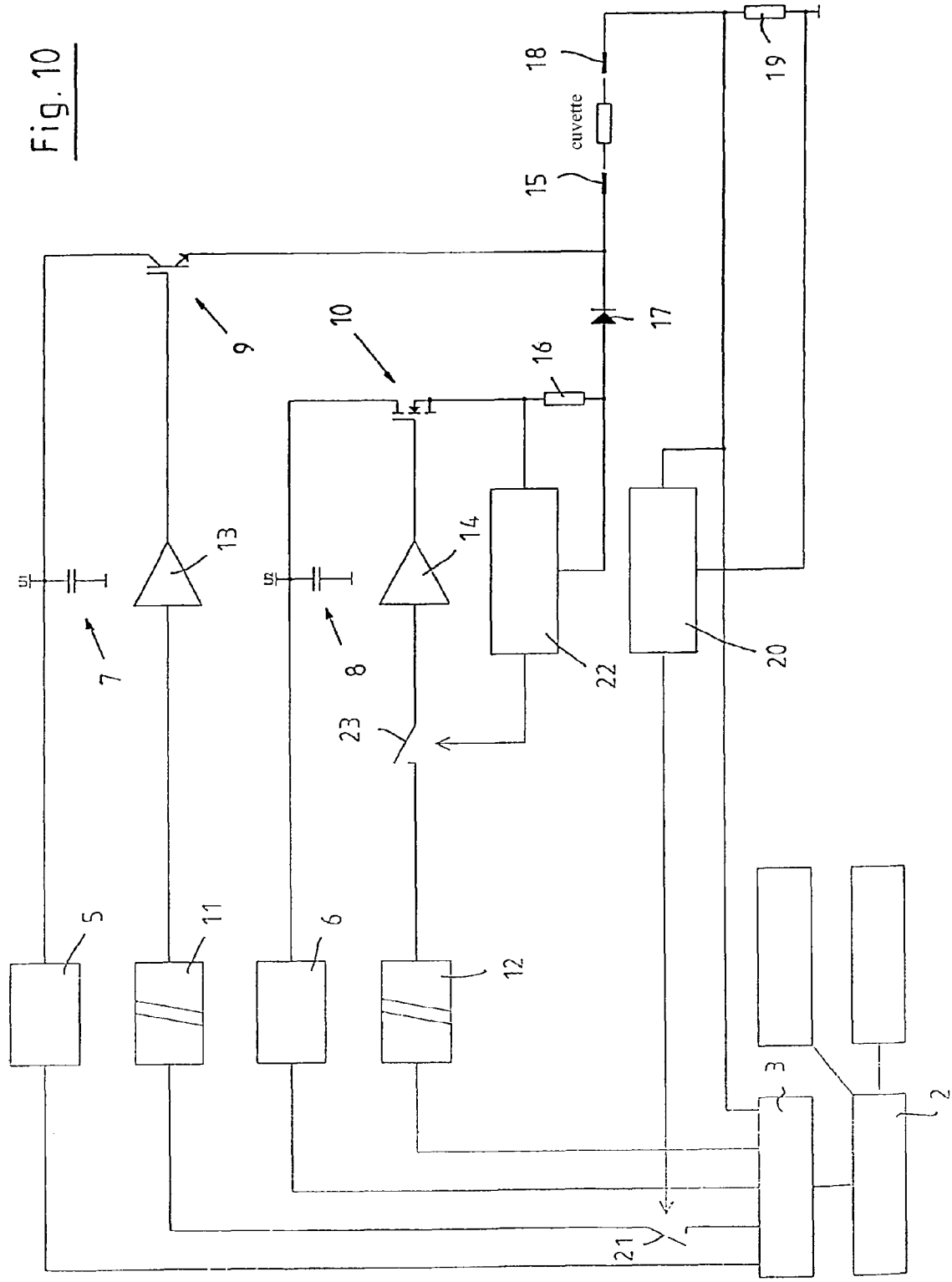
Figure 11:
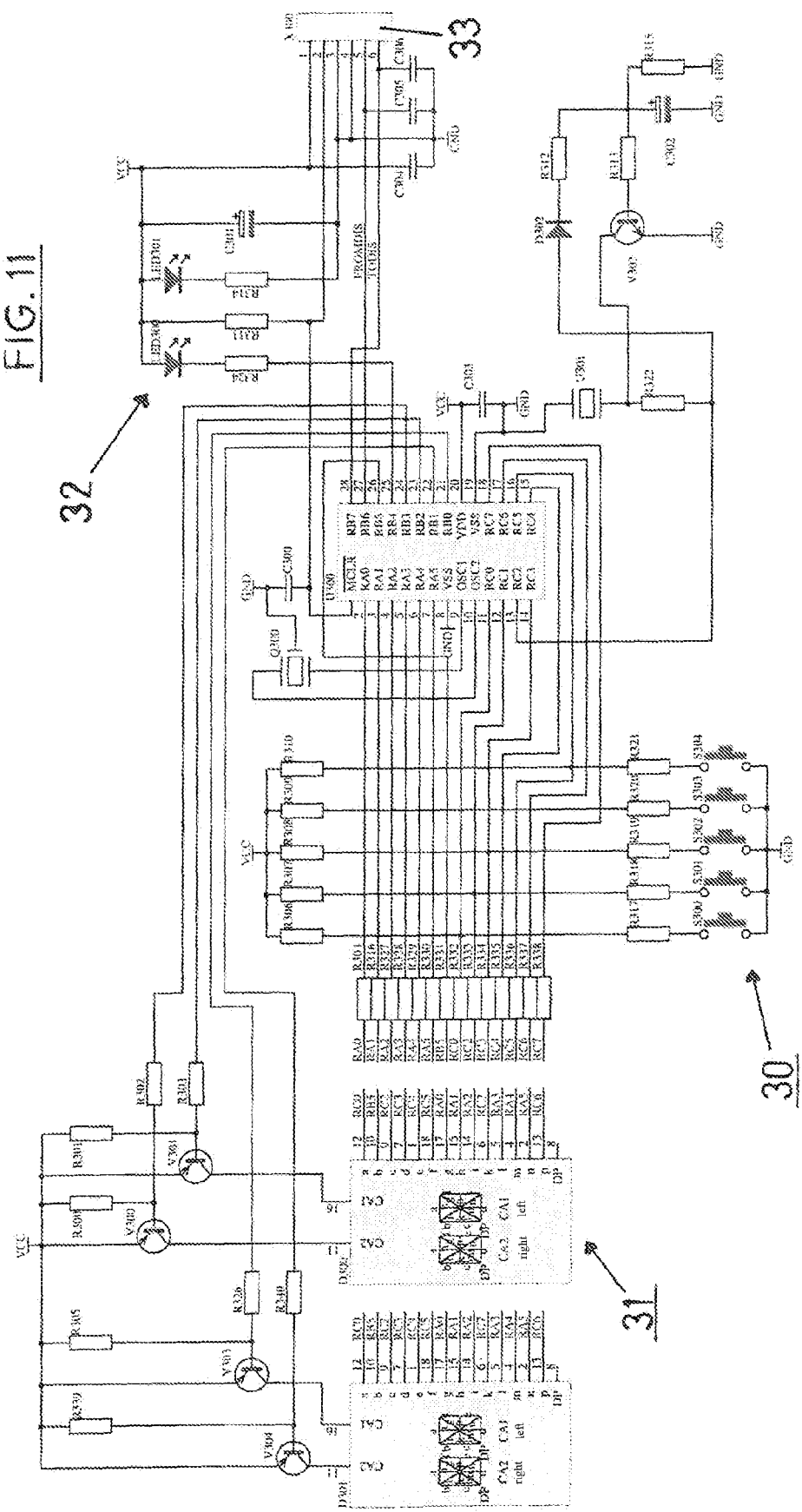
Figure 12:
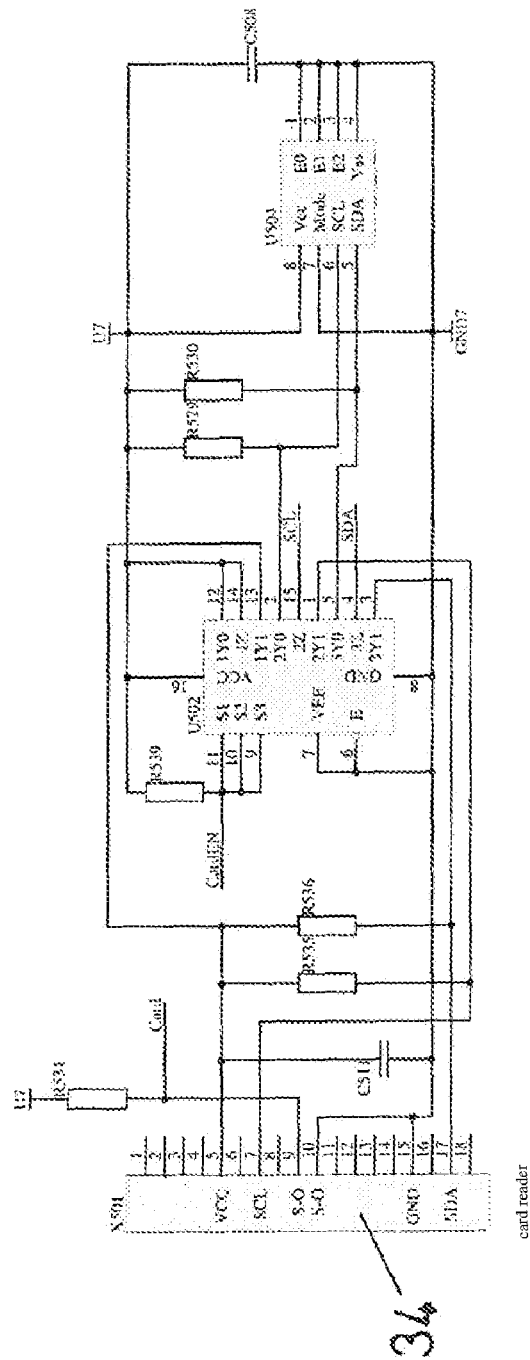
Figure 13:
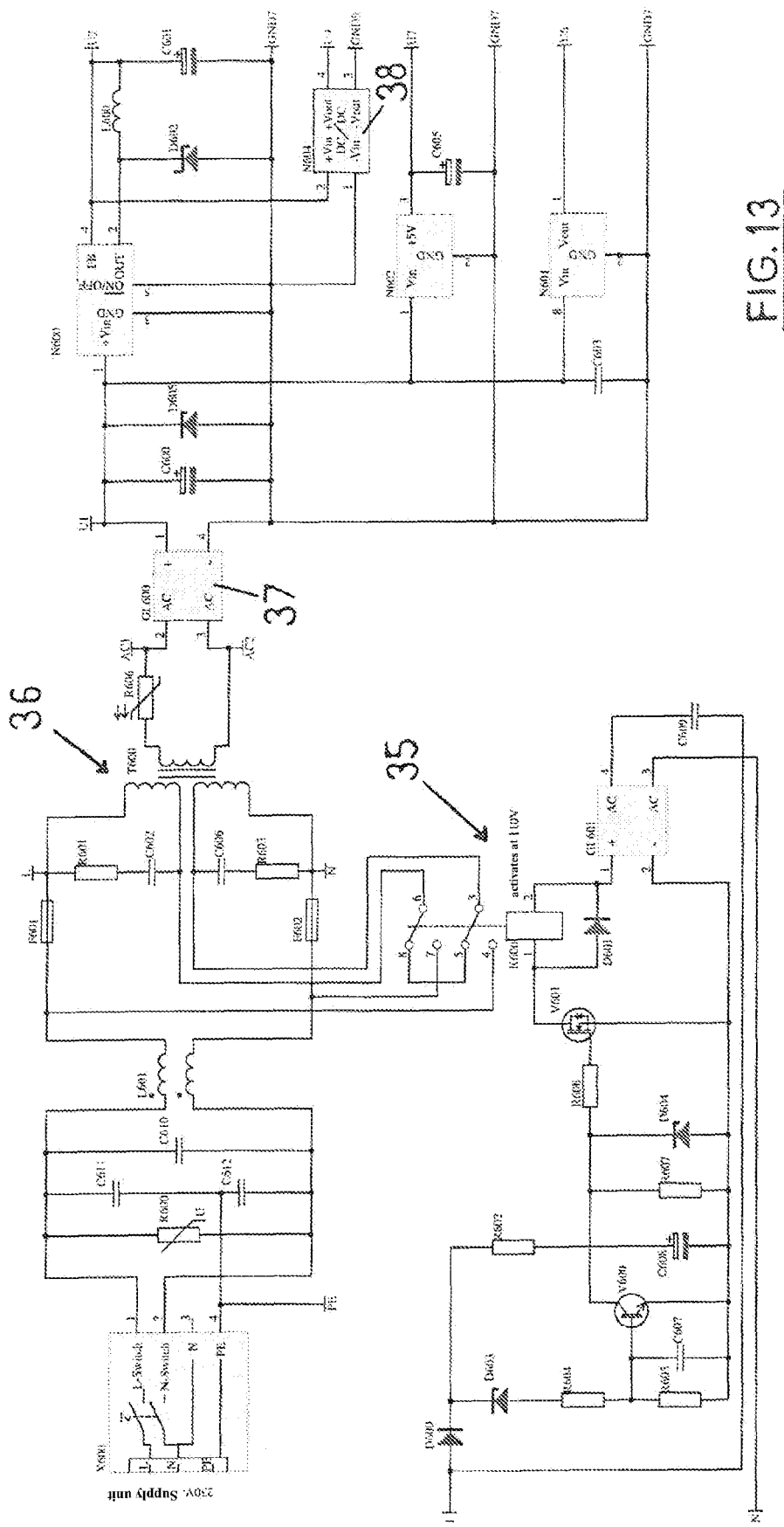
Figure 14:
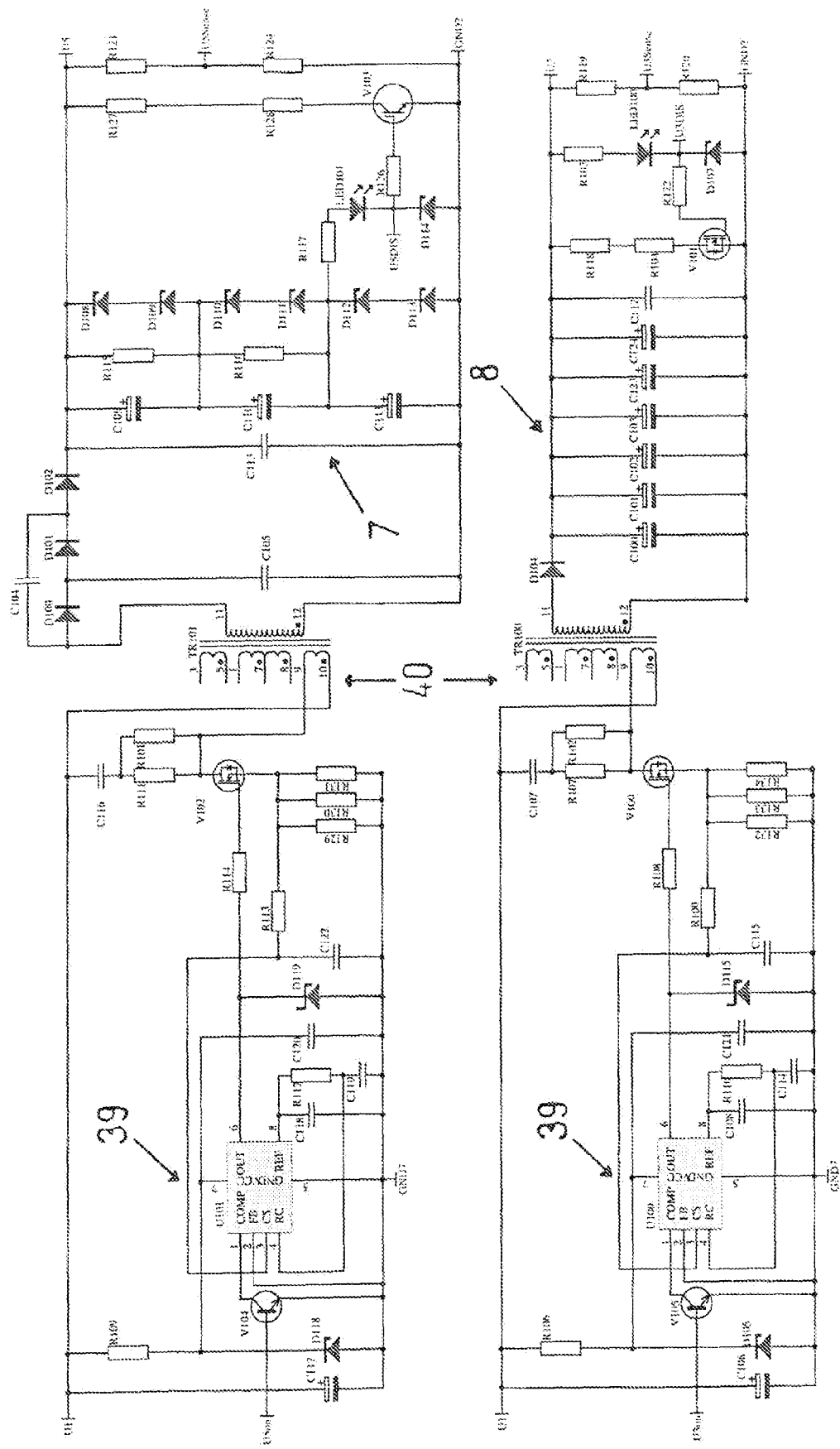
Figure 15:
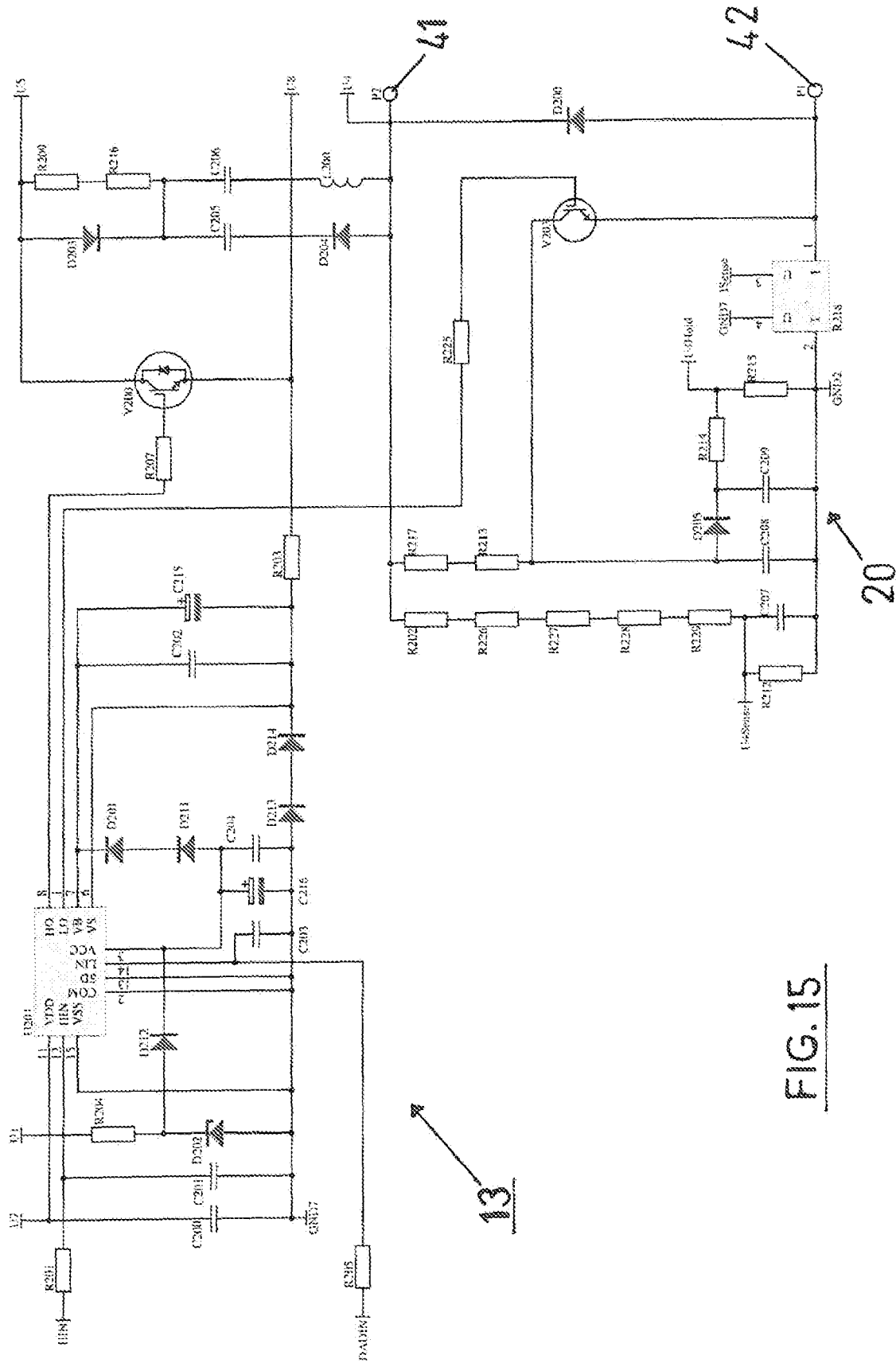
Figure 16:
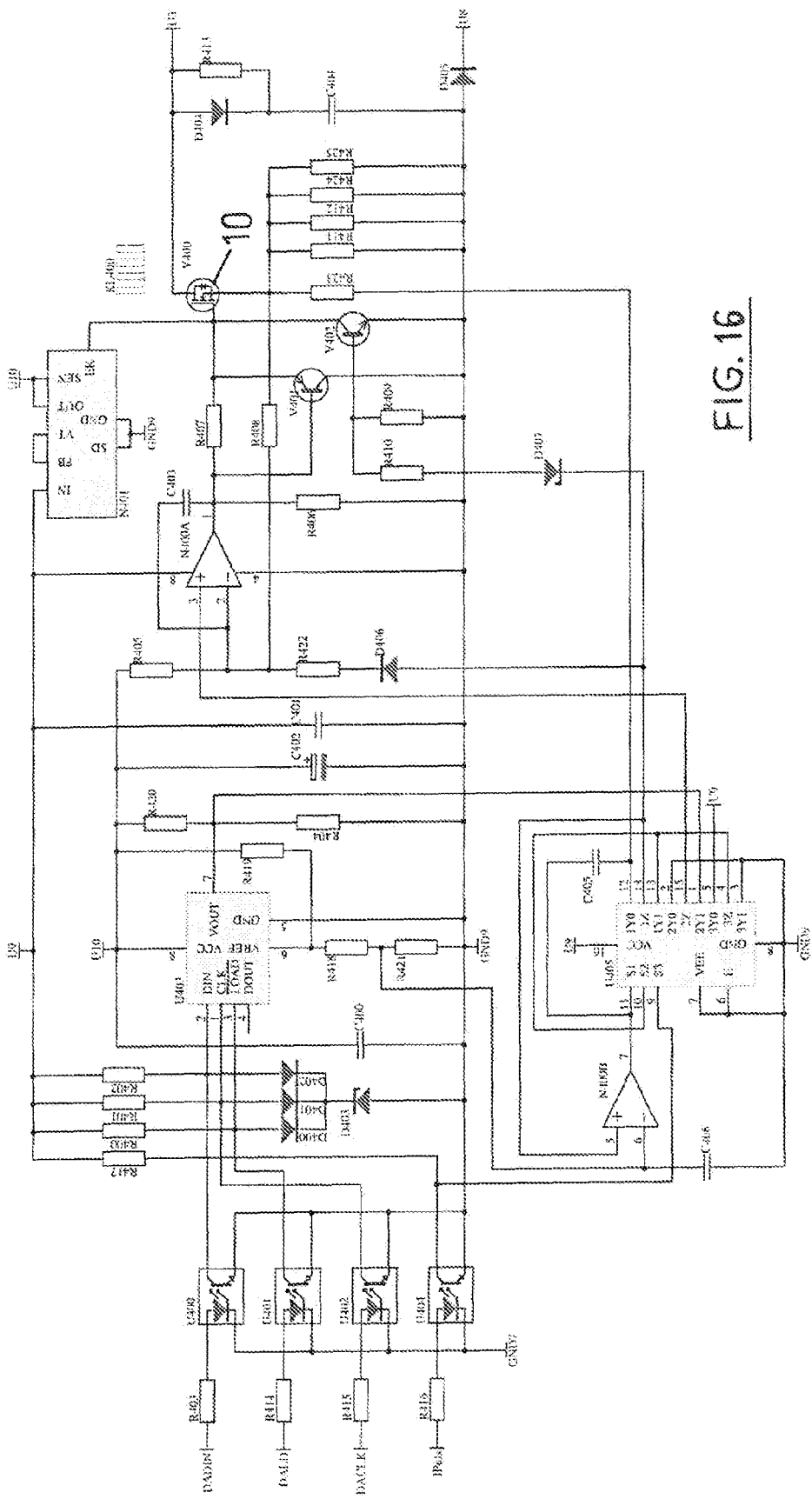
Figure 17:
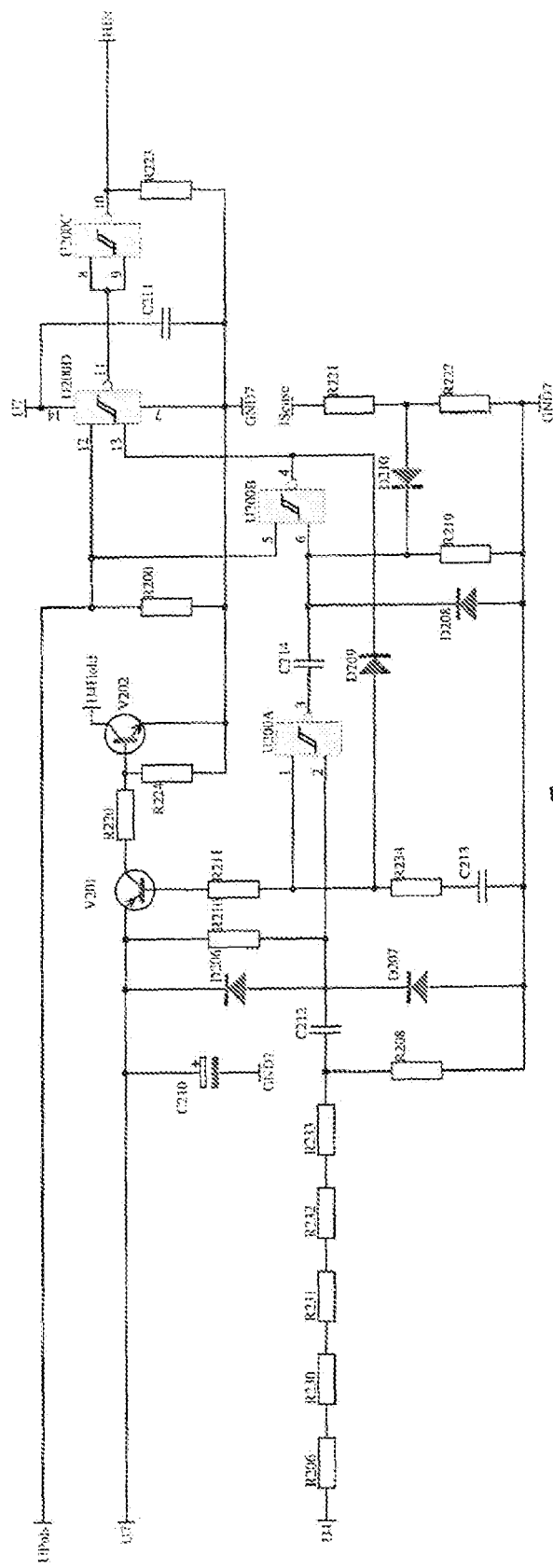
Figure 18:
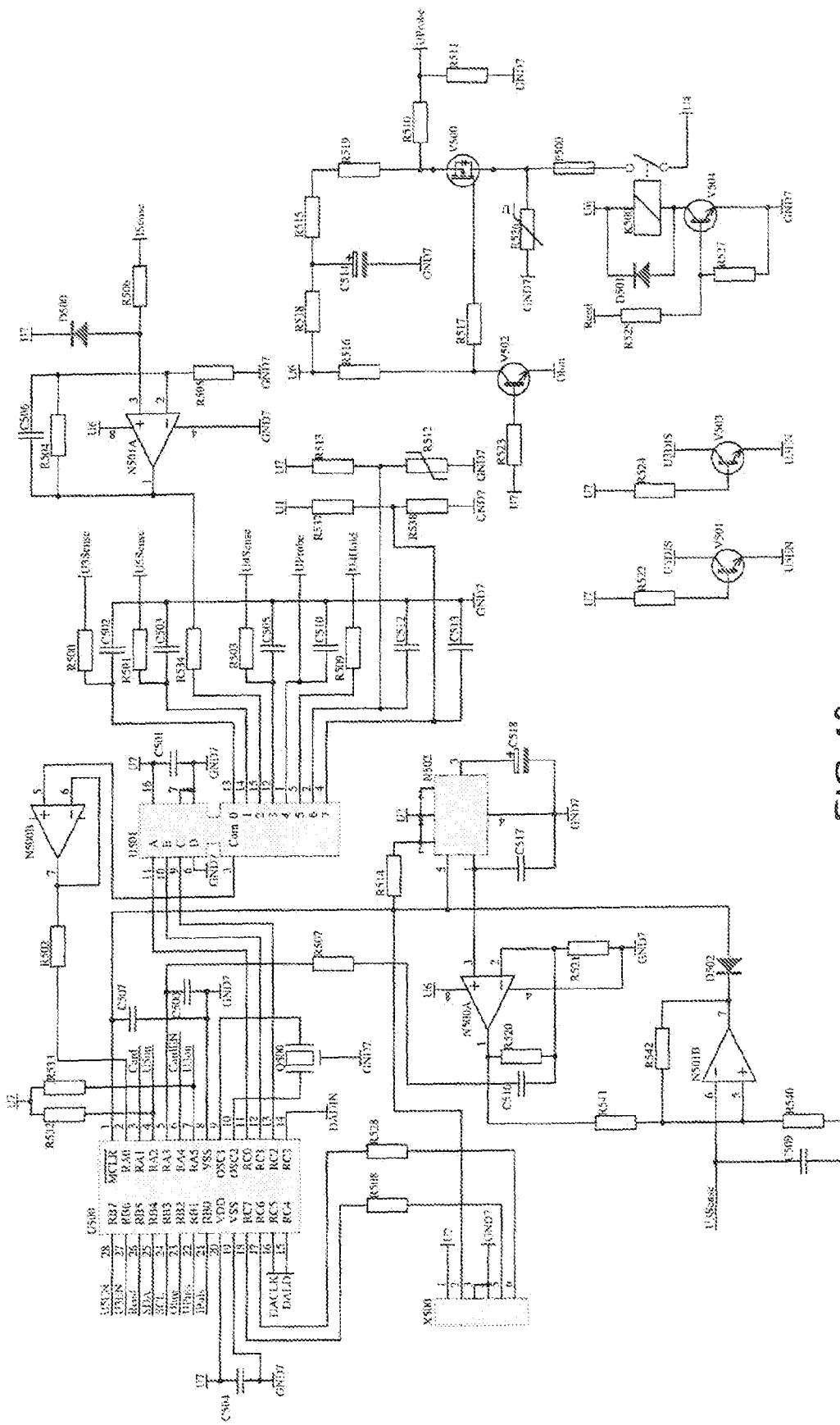
Figure 19:
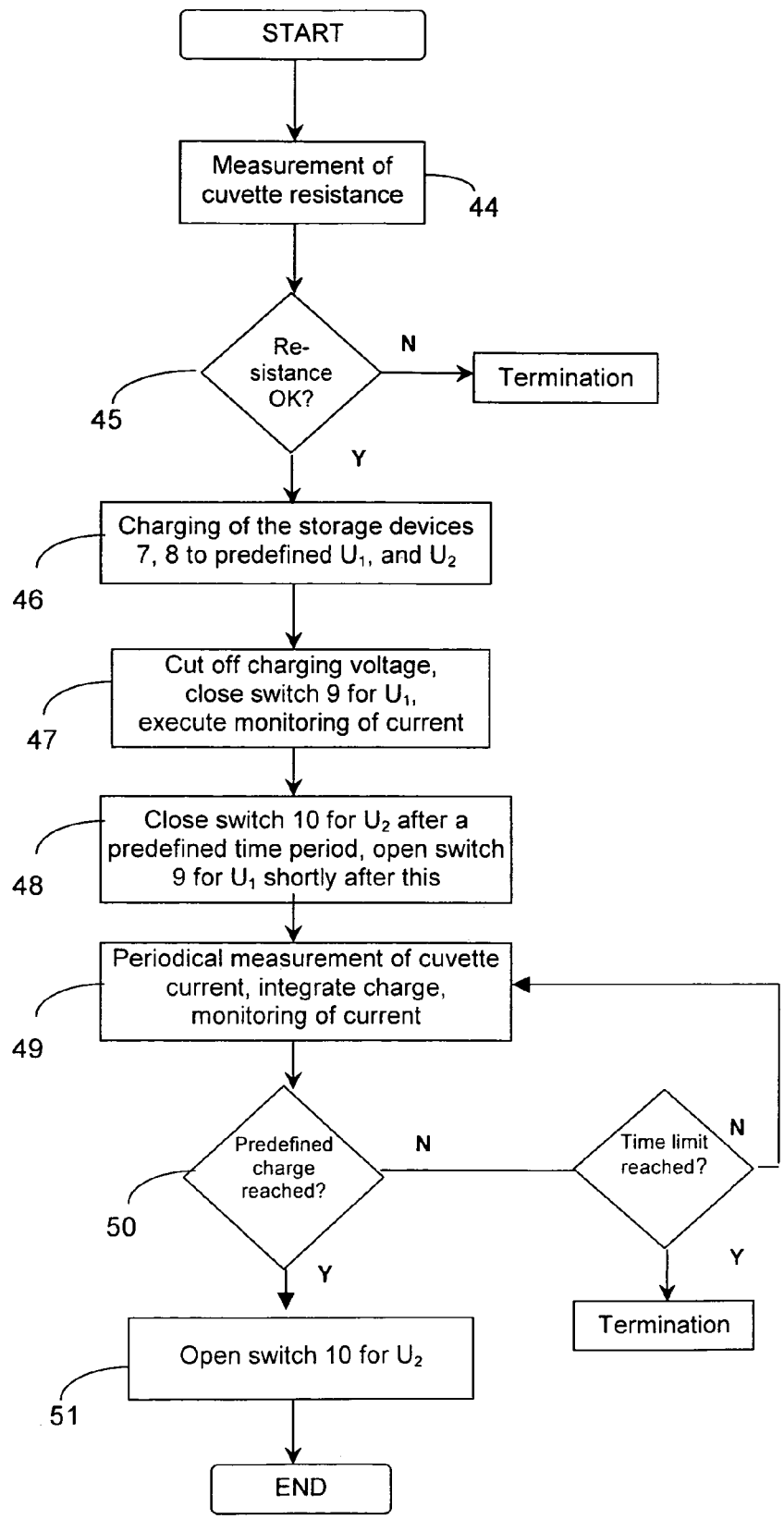

FIG. 1 shows a transfection of cytotoxic T cells from human blood,

FIG. 2 shows a transfection of pluripotent precursor cells from human blood, FIG. 3 shows a transfection of human neonatal dermal fibroblasts, FIG. 4 shows a transfection of human neonatal dermal melanocytes, FIG. 5 shows a transfection of human endothelial cells from the umbilical cord, FIG. 6 shows a transfection of the cell line K562 (analysis 4 h after transfection), FIG. 7 shows an investigation of the transfection efficiency as a function of the current intensity, pulse time and quantity of charge and of the expression intensity as a function of the quantity of charge, experiment using the CHO cell line, FIG. 8 shows an investigation of the transfection efficiency as a function of the current intensity, pulse time and quantity of charge and of the expression intensity as a function of the quantity of charge, experiment using the Jurkat cell line, FIG. 9 shows an investigation of the transfection efficiency as a function of the current intensity, pulse time and quantity of charge and of the expression intensity as a function of the quantity of charge, experiment using the Jurkat cell line and the surface marker protein H-2K$^k$, FIG. 10 shows a block diagram of an electroporator circuit, FIG. 11 shows a circuit diagram of a control panel, FIG. 12 shows a circuit diagram of a card reader, FIG. 13 shows a circuit diagram of a supply unit, FIG. 14 shows a circuit diagram of a HV power supply, FIG. 15 shows a circuit diagram of an HV switch, FIG. 16 shows a circuit diagram of a current regulating system, FIG. 17 shows a circuit diagram of a flash recognition system, FIG. 18 shows a circuit diagram of a control system, and FIG. 19 is a flow diagram to explain the sequence of the pulse delivery processes.

FIG. 1 shows the flow cytometric analysis of PBMC which had been transfected with H-2K$^k$-expression vector. The cells were successively incubated with digoxigenin-coupled anti-H-2K$^k$-antibody and Cy5-coupled anti-digoxigenin-antibody, as well as with a PerCP-coupled anti-CD8-antibody to identify human cytotoxic T cells and were analysed using a flow cytometer (FACScalibur, Becton Dickinson). (FL-2, FL-3=fluorescence channel 2, 3; SSC=sideward scatter, FSC=forward scatter, PerCP=peridinin chlorophyll protein, CD=cluster of differentiation).

FIG. 2 shows the flow cytometric analysis of CD34-positive stem cells enriched from PBMC which had been transfected with H-2K$^k$-expression vector. The cells were successively incubated with phycoerythin-coupled anti-H-2K$^k$-antibody, as well as with a APC-coupled anti-CD34-antibody to identify human CD34 positive haematopoietic stem cells and were analysed using a flow cytometer (FACScalibur, Becton Dickinson). (FL-1, FL-3=fluorescence channel 1, 3; SSC=sideward scatter, FSC=forward scatter, PE=phycoerythrin, APC=allophycocyanin, CD=cluster of differentiation).

FIG. 3 shows the flow cytometric analysis of human neonatal dermal fibroblasts (NHDF-Neo), which had been transfected with H-2K$^k$-expression vector. The cells were incubated with Cy5-coupled anti-H-2K$^k$ and analysed using a flow cytometer (FACScalibur, Becton Dickinson). (FL-1, FL-2, FL-3=fluorescence channel 1, 2, 3; SSC=sideward scatter, FSC=forward scatter).

FIG. 4 shows the flow cytometric analysis of human neonatal melanocytes (NHEM-Neo), which had been transfected with H-2K$^k$-expression vector. The cells were incubated with Cy5-coupled anti-H-2K$^k$ and analysed using a flow cytometer (FACScalibur, Becton Dickinson). (FL-1, FL-2, FL-3=fluorescence channel 1, 2, 3; SSC=sideward scatter, FSC=forward scatter).

FIG. 5 shows the flow cytometric analysis of endothelial cells from human umbilical cord (HUVEC), which had been transfected with H-2K$^k$-expression vector. The cells were incubated with Cy5-coupled anti-H-2K$^k$ and analysed using a flow cytometer (FACScalibur, Becton Dickinson). (FL-1, FL-2, FL-3=fluorescence channel 1, 2, 3; SSC=sideward scatter, FSC=forward scatter).

FIG. 6 shows the flow cytometric analysis of the human cell line K562 which had been transfected with H-2K$^k$-expression vector. The cells were incubated with Cy5-coupled anti-H-2K$^k$ and analysed using a flow cytometer (FACScalibur, Becton Dickinson). (FL-1, FL-2, FL-3=fluorescence channel 1, 2, 3; SSC=sideward scatter, FSC=forward scatter).

FIG. 7 shows a graphical representation of the transfection efficiency of CHO cells and the average fluorescence intensity (brightness) of the positive cells as a function of the quantity of charge Q which has flowed. The CHO cells were transfected with Cycle3-GFP expression vector and analysed after five hours using a flow cytometer (FACScalibur, Becton Dickinson). Closed circles correspond to a gradual increase in the pulse time for the same current intensity (2 A) or current density (4 A·cm$^{-2}$), open circles correspond to an increase in current intensity.

FIG. 8 shows a graphical representation of the transfection efficiency of Jurkat cells and the average fluorescence intensity (brightness) of the positive cells as a function of the quantity of charge Q which has flowed. The Jurkat cells were transfected with Cycle3-GFP expression vector and analysed after five hours using a flow cytometer (FACScalibur, Becton Dickinson). Closed circles correspond to a gradual increase in the pulse time for the same current intensity (2 A) or current density (4 A·cm$^{-2}$), open circles correspond to an increase in current intensity.

FIG. 9 shows a graphical representation of the transfection efficiency of Jurkat cells and the average fluorescence intensity (brightness) of the positive cells as a function of the quantity of charge Q which has flowed. The Jurkat cells were transfected with H-2K$^k$ expression vector and incubated after 3.5 hours with a Cy5-coupled anti-H-2K$^k$ and analysed using a flow cytometer (FACScalibur, Becton Dickinson). Closed circles correspond to a gradual increase in the pulse time for the same current intensity (2 A) or current density (4 A·cm$^{-2}$), open circles correspond to an increase in current intensity.

FIG. 10 shows a block diagram of the electroporator 1 with the necessary individual components. These comprise an adjusting unit 2, a control unit 3 to which a voltage supply unit 4 is connected as well as at least two HV power supplies 5, 6 with following storage devices 7, 8 and two power semiconductors 9, 10 provided for pulse delivery. The power semiconductors 9, 10 are controlled via a potential divider stage 11, 12 by the control unit 3 by means of an HV switch 13 and a regulating unit 14. The storage devices 7, 8 are directly connected to the inputs of the power semiconductors 9, 10, wherein the storage devices 7, 8 can consist of one or a plurality of capacitors depending on the field strength and the pulse duration. The power semiconductor 9 can for example consist of an IGBT and the power semiconductor 10 can consist of a MOSFET. However, the term "power semiconductor" should comprise all other electronic components or component assemblies by which means the voltages and currents to be switched within the scope of the invention can be switched with the required switching times. The output of the IGBT is directly connected to the cuvette connection 15 whereas the output of the MOSFET 10 is connected via a resistance 16 and a diode 17 to the cuvette connection 15 so that no pulse can flow back via the second power semiconductor 10 if both power semiconductors 9, 10 are controlled simultaneously. For this purpose the diode 17 is connected to the cuvette connection 15 on the cathode side. The second cuvette connection 18 is connected to earth via a resistance 19. The resistance 19 comprises a measuring shunt to measure the voltage drop and supply to an overcurrent switching stage 20. The overcurrent switching stage 20 can interrupt the pulse delivery by means of a switch 21 via the potential divider stage 11 and the HV switch 13 whereas a second overcurrent switching stage 22 interrupts a control system of the regulating unit 14 for the MOSFET 10 via a switch 23. The voltage applied via the resistance 16 is fed to the overcurrent switching stage 22 in order to bring about a current switchoff in the event that the maximum current is exceeded. Since the resistance 16 is located directly in the high-voltage circuit, the switch 23 is located after the potential divider stage 12 so that no high-voltage pulses can enter the control unit 3 and the operating staff are not endangered. In the case of the overcurrent switching stage 20, the low-resistance measuring resistance 19 lies behind the cuvette connections 15, 18 and is connected to earth so that the transmission of high-voltage pulses can be eliminated. Depending on the intended usage of the electroporator 1, one or a plurality of high-voltage power supplies 5, 6 with the relevant storage devices 7, 8 and the necessary potential divider stages 11, 12 and HV switch 13 or regulating unit 14 to control the power semiconductors 9, 10 can be used. The storage devices 7, 8 are equipped with one or a plurality of capacitors of the required capacity and breakdown voltage so that a suitably high quantity of charge can be stored and transferred to the cuvette connection 15.

The following FIGS. 11 to 18 shows the circuit diagrams of the individual components in the block diagram.

FIG. 11 shows a circuit diagram of the control panel for entering the parameter signals to be set wherein these can be preselected via a pushbutton switch 30 and checked visually using display elements 31. LEDs 32 shows when the equipment is ready for operation. The necessary parameters are prepared in the circuit and transmitted via a connector 33 to the control system in accordance with FIG. 14.

FIG. 12 shows a circuit diagram of a card reader 34 via which preset parameters for certain biological substances are read in and transmitted to the control unit as shown in FIG. 14.

FIG. 13 shows a circuit diagram of the supply unit which substantially consists of a 150/230 Volt changeover switch 35, a transformer stage 36 with primary-side wiring and voltage lead and secondary regulating stages to produce the necessary operating voltages. For this purpose a plurality of voltage regulators 38 are inserted after the rectifier 37.

FIG. 14 shows a circuit diagram of the two HV power supplies 5, 6 which can be identified from the block diagram. Both HV power supplies 5, 6 are acted upon by the voltage $U_1$ from the supply unit, wherein each regulating stage 39 receives a control signal U3on, U5on from the control system and the applied voltage $U_1$ charges the storage device 7, 8 consisting of a plurality of capacitors, in pulsed mode via a transformer stage 40. The desired voltage reached is transmitted via output signals U3sense, U5sense of the control system as shown in FIG. 15. The voltage $U_5$ of the storage device 7 is fed to an HV switch 13 as shown in FIG. 15 and the voltage $U_3$ of the storage device 8 is fed to a current regulating stage as shown in FIG. 16.

FIG. 15 shows a circuit diagram of the HV switch 13. The HV switch 13 receives the signal HIN generated by the pulse monitoring stage as shown in FIG. 16 to control the first power semiconductor 9. This transmits the applied voltage $U_5$ to a solder pad 41 for the HV cable for connecting the cuvette which is then connected to earth via a second solder pad 42 via a low-resistance measuring resistance. An overcurrent cutoff stage 20 delivers a control signal for the control unit as shown in FIG. 18 for switching off the power semiconductor 9 in the event of a preset maximum current rise being exceeded. The first solder pad 41 is further connected to the voltage output $U_4$ of the current regulating stage from FIG. 12 in order that a controlled current flow into the cuvette to deliver a specific quantity of charge can be achieved following the high-voltage pulse. The current regulating stage from FIG. 16 receives the control signals from the control unit from FIG. 18 via a potential divider stage and regulates the voltage $U_3$ applied to the storage device 8 to the voltage $U_4$ delivered via the solder pad 41. In this case, according to the invention, Q regulation or current regulation is used whereby the charge in the storage device 8 is determined at predefined time intervals of, for example, one millisecond and the delivered quantity of charge is determined taking into account the original charge.

FIG. 18 shows a circuit diagram of the control unit 3 which either takes into account the preset manual values or the values entered via a card reader 34 and controls the current regulating unit 14 as shown in FIG. 16 on the basis of further monitoring signals. The HV switch 13 as shown in FIG. 15 however is controlled after manually triggering the high-voltage pulse via a pulse monitoring stage 43 as shown in FIG. 17 so that after the HV pulse has been delivered, the quantity of charge can be monitored via the current regulating unit 14 as shown in FIG. 16.

The pulse parameters can thus on the one hand be preset manually and on the other hand via a card reader so that when a pulse is triggered manually via the existing regulating electronics, a high-voltage pulse with or without monitoring of the flowing current and if necessary, a continuous current signal with monitoring of the quantity of charge can be delivered via a second HV power supply.

FIG. 19 shows a schematic flow diagram of the operating sequence of a pulse delivery process controlled by the control unit 3 (see FIG. 10) according to a preferred embodiment of the invention. First, the required pulse parameters are predefined manually or by reading out a memory card (not shown). After starting the process (e.g. by actuating a corresponding trigger button), the ohmic resistance of the cuvette is first measured by briefly applying a low voltage (e.g. 12 V) to the cuvette connections 15, 18 and a subsequent current measurement (e.g. for 2 ms) in step 44. As part of the interrogation 45 it is checked whether this resistance lies within a predefined window. If not, the subsequent process is interrupted. The measured resistance is not used subsequently to calculate the charging voltage $U_2$ in the present embodiment of the invention. If the resistance lies in order within the predefined window, the storage devices 7, 8 are charged to the predefined voltages $U_1$ and $U_2$ in step 46. When the desired charging voltages are achieved, the charging by the HV power supplies 5, 6 is switched off. During the following pulse delivery, no recharging of the storage devices takes place. The pulse delivery for the high-voltage pulse then begins in step 47 by closing the semiconductor switch 9. As a result, a relatively high current flows through the cell. An excessively steep current rise is recognised by the overcurrent cutoff stage 20 and results in immediate opening of the switch 9 for safety reasons and interrupts the routine. In the present embodiment the high-voltage pulse is terminated after a predefined time of a few microseconds whereupon the second pulse follows immediately and without interruption. For this purpose in step 48 the second semiconductor switch 10 is already closed a short time before opening the first semiconductor switch 9 so that there is an interruption-free transition between the two pulses. In the short time interval in which both high-voltage switches 9, 10 are closed simultaneously, the diode 17 prevents any higher voltage from being able to flow from the storage device 7 into the storage device 8. The semiconductor switch 10 then remains open (provided that the maximum current is not exceeded by an overcurrent cutoff stage 22) until the predefined charge Q has flowed through the cuvette. For this purpose in step 49 the current flowing through the cuvette is measured and integrated in predefined time intervals (e.g. 1 ms). As soon as the predefined charge has been reached (see interrogation 50), the switch 10 is opened and the routine is terminated. The capacity of the storage device 8 is selected so that the voltage decreases gradually or slowly during the duration of the second pulse. If as a result of a fault, the predefined desired charge is still not yet achieved even when the storage device is almost completely discharged, the process will also be interrupted after a suitably selected time limit has been exceeded.

REFERENCE LIST

1 Electroporator
2 Adjusting unit
3 Control unit
4 Voltage supply unit
5 HV power supply
6 HV power supply
7 Storage device
8 Storage device
9 Power semiconductor
10 Power semiconductor
11 Potential divider stage
12 Potential divider stage
13 HV switch
14 Regulating unit
15 Cuvette connection
16 Resistance
17 Diode
18 Cuvette connection
19 Resistance
20 Overcurrent cutoff stage
21 Switch
22 Overcurrent cutoff stage
23 Switch
30 Push-button switch
31 Display element
32 LED
33 Connector
34 Card reader
35 Changeover switch
36 Transformer
37 Rectifier
38 Voltage regulator
39 Regulating stage
40 Transformer stage
41 Solder pad
42 Solder pad
43 Pulse monitoring stage
44 to 51 steps

The invention claimed is:

1. A circuit arrangement for introducing nucleic acids, peptides, proteins and/or other biologically active molecules into the cell nucleus of eukaryotic cells by means of electric current or for the treatment of cells, cell derivatives, subcellular particles and/or vesicles with electric current, the circuit arrangement comprising:

a first storage device for electrical charge;
a first high-voltage power supply configured to supply the first storage device;
a first power semiconductor configured to transfer a first quantity of charge of the first storage device into a suspension in a cuvette;
a second storage device for electrical charge;
a second high-voltage power supply configured to supply the second storage device;
a second power semiconductor configured to transfer a second quantity of charge of the second storage device into the suspension in the cuvette;
a current regulating unit coupled to the second semiconductor and configured to regulate charge transferred to the cuvette through the second power semiconductor; and
a control device for controlling the first power semiconductor and for controlling the second power semiconductor with the current regulating unit so as to:
charge the first storage device with a preset voltage (U1) and the second storage device with a voltage U2=R× I2×K2, where R is a resistance of the cuvette and the suspension therein, I2 is a desired current and K2 is a correction value which takes into account a property of the cuvette; and
transfer a first pulse with the voltage (U1) of the first storage device to the cuvette for a preset time;
wherein the control device is configured to determine a delivered quantity of charge in at least one selectable time interval, to compare a preset desired quantity of charge with the delivered quantity of charge, and to block at least one of the first and second power semiconductors on a reaching or exceeding of the desired quantity of charge.

2. The circuit arrangement as recited in claim 1 wherein the control device is configured to control the second power semiconductor with the current regulating unit so as to transfer, without interruption, at least one second pulse with the voltage (U2) of the second storage device to the cuvette.

3. The circuit arrangement as recited in claim 2 wherein the control device is configured to specify a switch-on time of the second pulse by the comparing the desired quantity of charge with the delivered quantity of charge delivered by a time of a measuring of the delivered quantity of charge and to specify a switch-off time of the second pulse at a reaching of the desired quantity of charge.

4. The circuit arrangement as recited in claim 3 wherein the control device is configured to determine the delivered quantity of charge with a measuring cycle of 1 msec, wherein the control device is configured, on a reaching of the desired quantity of charge, to block the second power semiconductor, and wherein during the switch-on time the voltage (U2) of the second storage device decreases exponentially.

5. The circuit arrangement as recited in claim 2 further comprising an overcurrent cutoff device configured to trigger a cutting off of at least one of the first and second pulse.

6. The circuit arrangement as recited in claim 1 wherein the control device is configured to determine the delivered quantity of charge using a difference between an original charge and a residual charge of at least one of the first and second storage devices.

7. The circuit arrangement as recited in claim 1 wherein the first pulse is a pulse of 2-10kV/cm having a duration of 10-100 µs as and a current density of at least 2 A·cm-2 and the control device is configured to control the second power semiconductor so as to transfer a second pulse having a current density of 2-14 A·cm-2 and a maximum duration of 100 ms without interruption.

8. The circuit arrangement as recited in claim 1 wherein the control device is configured to specify the at least one selectable time interval synchronous with a delivery of a charge of at least one of the first pulse, a second pulse and a further pulse.

9. The circuit arrangement as recited in claim 1 wherein the control device is configured, after at least one pre-determined time interval after the transfer of the first pulse, to measure a flowing current, and wherein the control device is configured, when the measured flowing current exceeds or falls below a desired value, to readjust a duration of the first pulse so as to control the delivered quantity of charge.

10. The circuit arrangement as recited in claim 1 wherein the control device is configured, after at least one pre-determined time interval after the transfer of the first pulse, to measure a flowing current, and wherein, the control device is configured, when the measured flowing current exceeds or falls below a desired value, to trigger an error message.

11. The circuit arrangement as recited in claim 1 wherein the control device is configured, after at least one pre-determined time interval after the transfer of the first pulse, to measure a flowing current, and wherein the control device is configured, when the measured flowing current exceeds or falls below a desired value, to readjust the desired value.

12. The circuit arrangement as recited in claim 1 wherein the control device is configured to receive pre-selected setting parameters of the first pulse including the voltage of the first storage device (U1) and the preset time of the transfer of the first pulse, the pre-selected setting parameters being inputted at least one of manually and by entering a code.

13. The circuit arrangement as recited in claim 1 further comprising a resistance measuring device configured to measure the resistance R of the cuvette before a controlling of at least one of the first and second power semiconductors.

14. The circuit arrangement as recited in claim 1 wherein the resistance R of the cuvette is predetermined.

15. The circuit arrangement as recited in claim 1 further comprising a card reader configured to read in, via a memory card, pre-selected setting parameters of the first pulse including the voltage of the first storage device (U1) and the preset time of the transfer of the first pulse.

16. The circuit arrangement as recited in claim 1 further comprising a measurement and recording device configured to measure and record a time profile of at least one of a voltage applied to the cuvette and a current flowing through and make the measured time profile available for storage on a memory card.

* * * * *